United States Patent
Kinley et al.

(10) Patent No.: US 7,504,245 B2
(45) Date of Patent: *Mar. 17, 2009

(54) BIOMASS CONVERSION TO ALCOHOL USING ULTRASONIC ENERGY

(75) Inventors: Michael T. Kinley, Waukee, IA (US); Bradley Krohn, Brandon, FL (US)

(73) Assignee: FCStone Carbon, LLC, West Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/954,657

(22) Filed: Sep. 30, 2004

(65) Prior Publication Data

US 2005/0136520 A1 Jun. 23, 2005

Related U.S. Application Data

(60) Provisional application No. 60/508,605, filed on Oct. 3, 2003.

(51) Int. Cl.
*C12P 7/06* (2006.01)
(52) U.S. Cl. ...................................................... 435/161
(58) Field of Classification Search ........................ None
See application file for complete search history.

(56) References Cited

U.S. PATENT DOCUMENTS

| | | | |
|---|---|---|---|
| 1,818,781 A | 8/1931 | Babonyi | |
| 2,307,725 A | 1/1943 | Daly et al. | |
| 2,631,111 A | 3/1953 | Meyer | |
| 2,776,228 A | 1/1957 | Snyder | |
| 2,951,776 A | 9/1960 | Scallet et al. | |
| 3,586,536 A | 6/1971 | Germino et al. | |
| 3,950,543 A | 4/1976 | Buffa et al. | |
| 3,971,306 A | 7/1976 | Wiese et al. | |
| 4,181,748 A | 1/1980 | Chwalek et al. | |
| 4,501,814 A | 2/1985 | Schoenrock et al. | |
| 4,517,022 A | 5/1985 | Harvey | |
| 4,624,805 A | 11/1986 | Lawhon | |
| 4,761,186 A | 8/1988 | Schara et al. | |
| 5,494,748 A | 2/1996 | Spehner | |
| 5,855,865 A | 1/1999 | Lambert et al. | |
| 5,859,236 A | 1/1999 | Burkart et al. | |
| 5,950,362 A | 9/1999 | Shors et al. | |
| 6,185,865 B1 | 2/2001 | Soll et al. | |
| 6,195,936 B1 | 3/2001 | Soll et al. | |
| 6,207,442 B1 | 3/2001 | Raymond et al. | |
| 6,250,011 B1 | 6/2001 | Soll et al. | |
| 6,254,914 B1 | 7/2001 | Singh et al. | |
| 6,333,181 B1 * | 12/2001 | Ingram et al. | 435/165 |
| 6,423,145 B1 * | 7/2002 | Nguyen et al. | 127/37 |
| 6,453,609 B1 | 9/2002 | Soll et al. | |
| 6,455,287 B1 | 9/2002 | Jem et al. | |
| 6,468,355 B1 | 10/2002 | Thompson et al. | |
| 6,566,125 B2 | 5/2003 | Johnston et al. | |
| 6,579,706 B2 | 6/2003 | Grae et al. | |
| 6,624,539 B1 * | 9/2003 | Hansen et al. | 310/26 |
| 6,899,910 B2 | 5/2005 | Johnston et al. | |
| 6,951,616 B2 | 10/2005 | Dahlberg | |
| 7,101,691 B2 | 9/2006 | Kinley et al. | |
| 2002/0155583 A1 | 10/2002 | Dale et al. | |
| 2003/0019736 A1 | 1/2003 | Garman | |
| 2003/0054500 A1 | 3/2003 | Ingram et al. | |
| 2003/0066899 A1 | 4/2003 | Gipson et al. | |
| 2003/0068415 A1 | 4/2003 | Taylor et al. | |
| 2003/0109011 A1 | 6/2003 | Hood et al. | |
| 2005/0118692 A1 | 6/2005 | Kinley et al. | |
| 2005/0233030 A1 | 10/2005 | Lewis et al. | |
| 2005/0239181 A1 | 10/2005 | Lewis et al. | |

(Continued)

FOREIGN PATENT DOCUMENTS

CA 2285312 10/1998

(Continued)

OTHER PUBLICATIONS

Iyer PV et al. Ammonia recycled percolation process for pretreatment of herbaceous biomass, Applied Biochemistry and Biotechnology, 1996, 57/58, pp. 121-132, entire document.*

(Continued)

*Primary Examiner*—Sandra Saucier
*Assistant Examiner*—Satyendra K Singh
(74) *Attorney, Agent, or Firm*—Schwegman, Lundberg & Woessner, P.A.

(57) ABSTRACT

A method comprising applying ultrasonic energy to a biomass to alcohol production process is provided. In one embodiment the alcohol production process is an ethanol production process. In one embodiment, the biomass to alcohol process employs ultrasonic energy as the only means of pretreatment. In one embodiment, the biomass to alcohol process additionally employs a concentrated acid hydrolysis pretreatment. In one embodiment, the biomass to alcohol process additionally employs any conventional pretreatment, such as a hydrothermal or chemical pretreatment, followed by an enzymatic hydrolysis step or a simultaneous enzymatic hydrolysis and saccharification step. In one embodiment, the conventional pretreatment is selected from the group consisting of dilute acid hydrolysis, high pressure hot water-based methods, i.e., hydrothermal treatments such as steam explosion and aqueous hot water extraction, reactor systems (e.g., batch, continuous flow, counter-flow, flow-through, and the like), ammonia explosion, ammonia recycled percolation (ARP), lime treatment and a pH-based process.

12 Claims, 8 Drawing Sheets

U.S. PATENT DOCUMENTS

| | | |
|---|---|---|
| 2006/0286654 A1 | 12/2006 | Kinley et al. |
| 2007/0037267 A1 | 2/2007 | Lewis et al. |
| 2007/0178567 A1 | 8/2007 | Lewis |
| 2007/0202214 A1 | 8/2007 | Lewis et al. |
| 2008/0096261 A1 | 4/2008 | Kinley et al. |

FOREIGN PATENT DOCUMENTS

| | | |
|---|---|---|
| EP | 0589303 A1 | 3/1994 |
| SU | 724567 | 3/1980 |
| WO | WO-98/45418 A1 | 10/1998 |
| WO | WO-00/71266 A1 | 11/2000 |
| WO | WO-01/83102 A3 | 11/2001 |
| WO | WO-2004081193 A2 | 9/2004 |
| WO | WO-2005/021742 A2 | 3/2005 |
| WO | WO-2007/012069 A2 | 1/2007 |

OTHER PUBLICATIONS

Sun Y. & Cheng J. Hydrolysis of lignocellulosic materials for ethanol production: a review, Bioresource Technology, 2002, 83: 1-11, entire document.*

Barton, S., et al., "The Effects of Ultrasound on the Activities of Some Glycosidase Enzymes of Industrial Importance", *Enzyme and Microbial Technology*, 18 (3), (Feb. 15, 1996),190-194.

Imani, M., et al., "High-Performance Hydrolysis of Cellulose Using Mixed Cellulase Species and Ultrasonication Pretreatment", *Biochemical Engineering Journal*, 17, (2004),79-83.

Klanarong, S., et al., "Processing of Cassava Waste for Improved Biomass Utilization", *Bioresource Technology*, 71 (1), (2000),63-69.

Singh, Vijay, et al., "Modified Dry Grind Ethanol Process", *Publication of the Agricultural Engineering Department University of Illinois at Urbana—Champaign UILU No. 2001-7021*, (Jul. 18, 2001),1-43.

Sosulski, F. W., et al., "Wet Milling and Separation of Wheat Distillers' Grains with Solubles into Dietary Fiber and Protein Fractions", *Cereal Chemistry, American Association of Cereal Chemists*, 68 (6), (1991),562-565.

Wood, B. E., et al., "Ultrasound Stimulates Ethanol Production During the Simultaneous Saccharification and Fermentation of Mixed Waste Office Paper", *Boitechnology Progress*, 13 (3), XP-002071668,(May 1997),232-237.

"PCT Application No. PCT/US2004/027866, International Preliminary Report on Patentability mailed Mar. 9, 2006", 6 pgs.

"Prosecution File History for U.S. Appl. No. 10/926,783", 137 pgs.

Kinley, M. T., et al., "Biomass Conversion to Alcohol Using Ultrasonic Energy", U.S. Appl. No. 11/974,757, filed Oct. 16, 2007.

"U.S. Appl. No. 10/926,783, Amendment After Notice of Allowance filed Jun. 9, 2006", 22 pgs.

"U.S. Appl. No. 10/926,783, Preliminary Amendment filed Apr. 26, 2005", 21 pgs.

"U.S. Appl. No. 10/926,783, Response filed Jul. 21, 2005 to Restriction Requirement mailed Jun. 27, 2005", 22 pgs.

"U.S. Appl. No. 10/926,783, Response to Rule 312 Communication mailed Jun. 19, 2006", 2 pgs.

"U.S. Appl. No. 10/926,783, Restriction Requirement mailed Jun. 27, 2005", 9 pgs.

"U.S. Appl. No. 10/926,783, Non Final Office Action mailed Oct. 18, 2005", 24 pgs.

"U.S. Appl. No. 10/926,783, Notice of Allowance mailed May 15, 2006", 11 pgs.

"U.S. Appl. No. 10/926,783, Response filed Feb. 18, 2006 to Non Final Office Action mailed Oct. 18, 2005", 27 pgs.

"U.S. Appl. No. 11/449,089, Non-Final Office Action mailed Jul. 3, 2008", 16 pgs.

"U.S. Appl. No. 11/449,089, Preliminary Amendment filed Oct. 19, 2007", 8 pgs.

"U.S. Appl. No. 11/449,089, Response filed Feb. 26, 2008 to Non-Final Office Action mailed Nov. 28, 2007", 18 pgs.

"U.S. Appl. No. 11/449,089 Non-Final Office Action mailed Nov. 28, 2007", 21 pgs.

"Canadian Patent Application No. 2,536,991, Response filed Jun. 6, 2007 to Official Action dated Dec. 5, 2006", 36 pgs.

"Canadian Patent Application No. 2,536,991, Office Action mailed Dec. 5, 2006", 5 pgs.

Chisti, Y., "Sonobioreactors: using ultrasound for enhanced microbial productivity", *Trends in Biotechnology*, 21(2), (2003), 89-93.

"Biomass Program: Theorectical Ethanol Yield Calculator", [online]. [archived Dec. 9, 2004]. Retrieved from the Internet: <URL: http://web.archive.org/web/20041209072504/http://www.eere.energy.gov/biomass/ethanol_yield_calculator.html>, ((last updated Jun. 22, 2004)), 2 pgs.

\* cited by examiner

BIOMASS CONVERSION TO ALCOHOL USING ULTRASONIC ENERGY

CROSS-REFERENCE TO RELATED APPLICATION

This application claims the benefit under 35 U.S.C. 119 (e) of U.S. Provisional Application No. 60/508,605 filed on Oct. 3, 2003, which is hereby incorporated by reference in its entirety.

FIELD

The present subject matter relates generally to biomass conversion to alcohol, and, more particularly, to biomass conversion to alcohol using ultrasonic energy.

BACKGROUND

The methods for producing various types of alcohol from grain generally follow similar procedures, depending on whether the process is operated wet or dry. One alcohol of great interest today is ethanol. Ethanol can be produced from virtually any type of grain, but is most often made from corn.

Since its inception, the national market for fuel ethanol has grown from about 6.6 million liters (about 175 million gallons (gal)) in 1980 to about 7.9 billion liters (about 2.1 billion gal) in 2002. In 2003, the U.S. ethanol industry produced a record 10.6 billion liters (about 2.8 billion gal), all of which was produced from 74 ethanol plants located mainly within the corn-belt. Recent federal government legislation has been proposed, which would mandate that ethanol production capacity grow to approximately 1.9 trillion liters (approximately five (5) billion gal) by 2012. Consequently, ethanol producers are seeking methods to improve yields before incurring the high capital costs of direct plant expansion. Because of the ongoing need for ethanol, as well as recent and expected future rapid growth of the ethanol industry, producers are finding it difficult to incur the time and expense required to refine existing technologies to meet the potentially mandated increases and also remain cost competitive with intense ethanol producer competition. Higher yields are also desired for other types of alcohol.

Alcohols such as ethanol can be produced from virtually any type of grain, but ethanol in particular is most often made from corn, which contains high levels of starches that can be broken down into the glucose sugars needed for traditional fermentation. However, there is a growing interest in producing alcohol from other sources, such as cellulose, a linear polymer of glucose molecules. Cellulose is a desirable alternative over other ethanol feedstocks such as corn grain since it is renewable, abundant, does not take away from the food supply and is available at a relatively low cost. However, there are several known difficulties associated with efficiently converting the cellulose (contained in biomass) to glucose sugars, including the extensive chemical treatment required and the high capital and energy costs involved.

The biggest challenge for a commercial biomass-to-alcohol process is the ability to cost-effectively convert hemicellulose and cellulose to fermentable sugars. The combination of hemicellulose and lignin provide a protective sheath around the cellulose, which must be modified or removed before efficient hydrolysis of cellulose can occur. Furthermore, the cellulose must be decrystallized or "softened" before it can be processed into alcohol. Softening entails insertion of water into the crystalline structure of the cellulose, thereby opening up or loosening its structure such that it can be economically converted to glucose for fermentation.

The pretreatment softening process also usually includes hydrolysis of hemicellulose to pentose sugars, which precedes enzyme or acid hydrolysis of the cellulose to glucose. However, pretreatment-hydrolysis of plant biomass can often result in the creation and release of other chemicals that inhibit microbial fermentation. These inhibitors (i.e. furfural) are largely the product of sugar degradation, and methods to remove these inhibitors or to reduce their formation are needed.

Biomass conversion to alcohol also poses unique fermentation considerations. The *Saccharomyces cerevisiae* yeast strains used in conventional corn ethanol plants for example, can ferment glucose, but can not ferment pentose sugars such as xylose. Additionally, there is currently no naturally occurring microorganism that can effectively convert all the major sugars present in plant biomass to ethanol. Therefore, genetically engineered yeast or bacteria, which can ferment both glucose and xylose to alcohol are being used for biomass to alcohol processes. However, genetically-enhanced recombinant strains of fermentative microorganisms, including recombinant strains of yeast, bacteria and fungi, as well as transgenic nucleic acids (DNA, RNA) derived from such component may pose environmental disposal and permitting problems. Methods to remove these components in product and waste streams are needed.

For the reasons stated above, and for other reasons stated below which will become apparent to those skilled in the art upon reading and understanding the present specification, there is a significant need in the art for systems and methods that provide for improved biomass conversion to alcohol, such as ethanol, in a cost-effective manner.

SUMMARY

A method comprising applying ultrasonic energy to a biomass to alcohol production process is provided. In one embodiment the alcohol production process is an ethanol production process. In one embodiment, the biomass to alcohol process employs ultrasonic energy as the only means of pretreatment. In one embodiment, the biomass to alcohol process additionally employs a concentrated acid hydrolysis pretreatment. In one embodiment, the biomass to alcohol process additionally employs a two-stage acid hydrolysis pretreatment (commonly referred to as a "two-stage acid hydrolysis process"). In one embodiment, the biomass to alcohol process additionally employs any conventional pretreatment, such as a hydrothermal or chemical pretreatment, followed by an enzymatic hydrolysis step or a simultaneous enzymatic hydrolysis and saccharification step. In one embodiment, the conventional pretreatment is selected from the group consisting of dilute acid hydrolysis, high pressure hot water-based methods, i.e., hydrothermal treatments such as steam explosion and aqueous hot water extraction, reactor systems (e.g., batch, continuous flow, counter-flow, flow-through, and the like), ammonia explosion, ammonia recycled percolation (ARP), lime treatment and a pH-based process.

A pretreatment method comprising applying ultrasonic energy to a biomass slurry wherein the ultrasonic energy causes an increase in conversion rates of components in the biomass slurry to fermentable sugars is also provided. In one embodiment, at least a portion of the biomass slurry is hydrolyzed during the pretreatment step. In one embodiment, the components are cellulose and hemicellulose. In one embodiment, the fermentable sugars are converted into alcohol.

In one embodiment ultrasonic energy is applied before, during and/or after a conventional pretreatment step. In one embodiment, ultrasonic energy is additionally or alternatively applied after fermentation, such as to the thin stillage component.

A system comprising one or more ultrasonic energy transducers and a biomass to alcohol production facility adapted for use with the one or more ultrasonic energy transducers is also provided. In one embodiment, the biomass to alcohol system employs ultrasonic energy as the only means of pretreatment. In one embodiment, the biomass to alcohol system additionally employs a concentrated acid hydrolysis pretreatment. In one embodiment, the biomass to alcohol system additionally employs a two-stage acid hydrolysis pretreatment. In one embodiment, the biomass to alcohol system additionally employs any conventional pretreatment, such as a hydrothermal or chemical pretreatment, followed by an enzymatic hydrolysis step or a simultaneous enzymatic hydrolysis and saccharification step.

Although the systems and methods described herein focus primarily on ethanol production from plant biomass, it is intended that any of the systems and methods described herein can be used in virtually any alcohol production facility and with any suitable type of biomass.

In one embodiment, systems and methods for improving biomass conversion to alcohol using ultrasonic energy are provided. The particular improvement achieved depends on several factors, including, but not limited to, the particular point in the process at which the ultrasonic energy is applied, the type of biomass being used, type of additional pretreatment methods, if any, being employed, and so forth. The manner in which the ultrasonic energy is applied can also affect the end result. This includes, but is not limited to, the frequency of ultrasonic energy applied, the power and intensity at which the ultrasonic energy is applied, the length of time the ultrasonic energy is applied, the location of the transducer within the medium to be treated, and so forth. In one embodiment, high-powered ultrasonic (HPU) energy is used.

The particular benefit obtained will vary depending on whether a conventional ultrasonic horn known in the art is used or whether another type of horn is used, such as a cascade type horn (which is known to increase the area of cavitation bubble generation), and the like. Other factors particular to the operation can also affect the benefit obtained. This includes, but is not limited to, the flow rate of the fluid medium, the nature of the medium to be acted upon, including type and amount of particulate content, temperature, and so forth.

Ultrasonication of biomass is highly effective at the complex destructuring, disaggregation, and depolymerization (i.e., hydrolysis or breakdown to sugars and/or intermediate chains of sugars) of hemicellulose and cellulose. Ultrasonication of biomass in specific locations in the biomass to alcohol process has the potential to interface or be integrated with existing biomass pretreatment technologies allowing technological hurdles, process inefficiencies and/or poor economics to be overcome. Alternatively, ultrasonication of biomass before, during and/or just after pretreatment during the biomass to alcohol process may also function as a standalone, highly efficient, and economic pretreatment process for ethanol production.

Some of the advantages of ultrasonication as a biomass pretreatment enabling technology, or as a stand-alone biomass pretreatment process, for alcohol production include, but are not limited to, the ability of ultrasonication to:

produce highly digestible cellulose solids that can achieve high glucose yields with low enzyme loadings, resulting in lower cellulase costs;

possibly eliminate the need for acid during pretreatment, while generating high sugar yields;

reduce and even possibly eliminate the need for chemicals during both pretreatment and pre-fermentation conditioning, which will have the additional advantages of lowering the cost of materials of construction because of a less corrosive environment and minimizing of the formation of degraded sugars and subsequent production of chemical such as furfural which inhibit microbial fermentation;

reduce heat and energy demands, which will also have the advantage of minimizing formation of degraded sugars and subsequent production of chemicals such as furfural which inhibit microbial fermentation;

create low water usage due to highly effective destructuring and disaggregation of hemicellulose, cellulose and lignin; and possibly optimize settings in flowrate, temperature, and acid level to maximize hemicellulose recovery and lignin removal with water or dilute acid solutions in flow-through reactor systems.

The novel system and methods described herein are expected to increase overall yields of alcohol, such as ethanol, by at least 10% up to 100% or more. Glucose yields will also increase by at least 10% up to 100% or more. Yields of other sugars are also expected to increase. Actual yields are dependent on many factors including, but not limited to, type of biomass feedstock used, type of pretreatment methods being employed, and so forth. Additionally, when used after fermentation, ultrasonic energy can also significantly decrease the presence of unwanted genetically engineered materials in product and waste streams, such as the feed molasses stream, in some instances reducing the amounts to undetectable levels.

DETAILED DESCRIPTION

Figure 1:
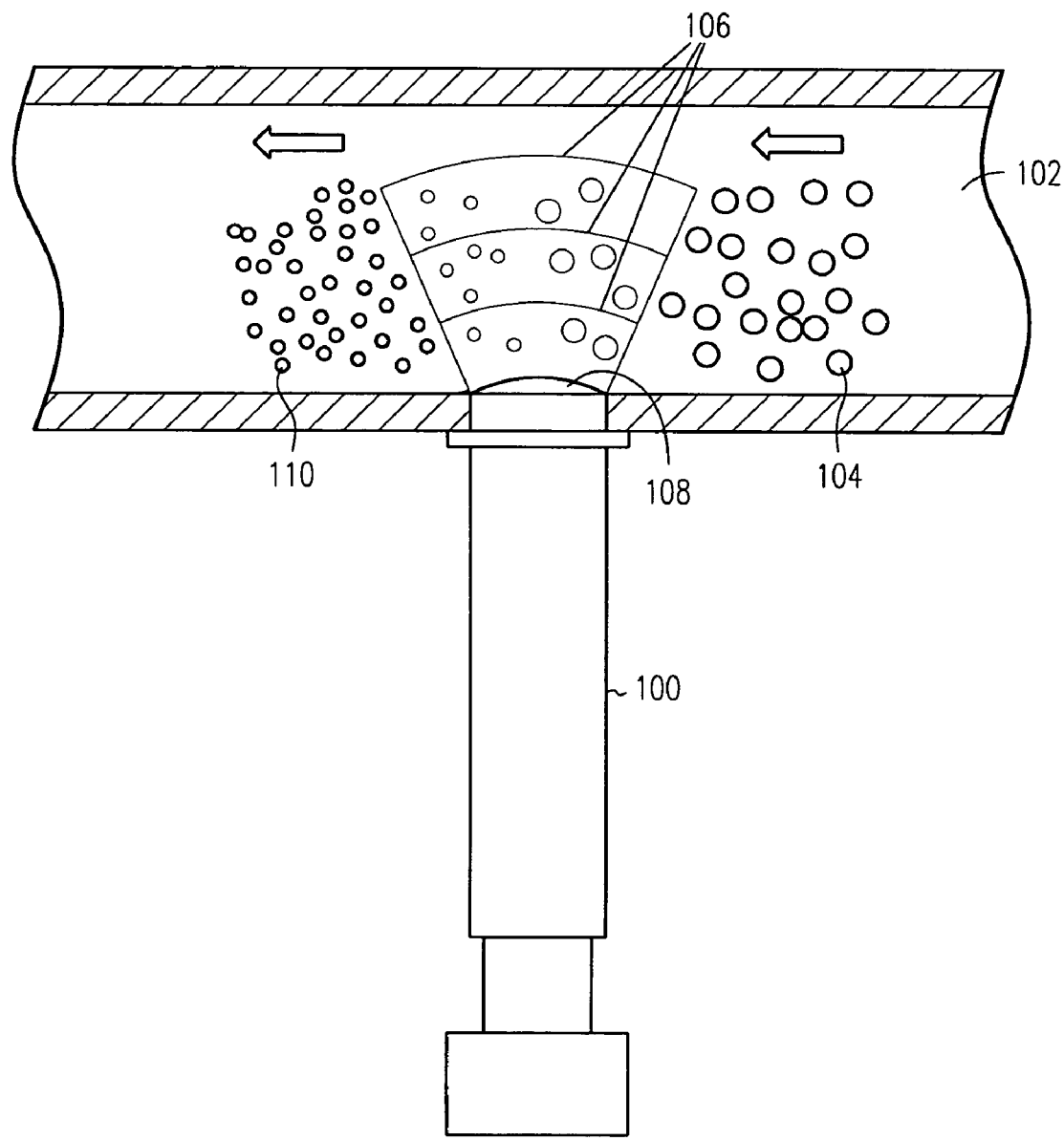
FIG. 1 is a simplified illustration of an ultrasonic transducer located in a process flow stream in one embodiment of the present invention.

In the following detailed description of embodiments of the invention, reference is made to the accompanying drawings that form a part hereof, and in which is shown by way of illustration specific preferred embodiments in which the subject matter may be practiced. These embodiments are described in sufficient detail to enable those skilled in the art to practice them, and it is to be understood that other embodiments may be utilized and that mechanical, chemical, structural, electrical, and procedural changes may be made without departing from the spirit and scope of the present subject matter. The following detailed description is, therefore, not to be taken in a limiting sense, and the scope of embodiments of the present invention is defined only by the appended claims.

The present invention provides systems and methods of improving biomass conversion to alcohol using ultrasonic energy in specific locations in virtually any biomass to alcohol process. Each of these methods can also optionally utilize a conventional pretreatment step. Ultrasonic energy applied before during and/or after a pretreatment step or as a pretreatment step by itself, enables a greater conversion rate of cellulose and hemicellulose as compared with conventional methods, resulting in higher conversion of the resulting sugars to alcohol during fermentation. In one embodiment, ultrasonication is additionally or alternatively used after fermentation to destroy contaminating recombinant fermentative microorganisms and to degrade, hydrolyze or denature any transgenic nucleic acids (derived from recombinant fermentative microorganisms) present in waste and/or product streams after fermentation. Other benefits can also be realized which will become apparent herein.

The Detailed Description that follows begins with a brief definition section, followed by discussions on biomass conversion to alcohol and on ultrasonic energy technology useful herein. This is followed by a detailed description of specific embodiments of the invention which includes a discussion of the various benefits of the use of ultrasonic energy at different points in specific biomass to alcohol processes.

Definitions

The term "biomass" is intended herein to refer to any non-fossilized, i.e., renewable, organic matter collected for use as a source of energy. The various types of biomass include plant biomass (defined below), animal biomass (any animal by-product, animal waste, etc.) and municipal waste biomass (residential and light commercial refuse with recyclables such as metal and glass removed).

The term "plant biomass" or "ligno-cellulosic biomass" as used herein is intended to refer to virtually any plant-derived organic matter (woody or non-woody) available for energy on a sustainable basis. "Plant-derived" necessarily includes both sexually reproductive plant parts involved in the production of seed (e.g., flower buds, flowers, fruit and seeds) and vegetative parts (e.g., leaves, roots, leaf buds and stems). Plant biomass can include, but is not limited to, agricultural crop wastes and residues such as corn stover, wheat straw, rice straw, sugar cane bagasse and the like. Plant biomass further includes, but is not limited to, woody energy crops, wood wastes and residues such as trees, softwood forest thinnings, barky wastes, sawdust, paper and pulp industry waste streams, wood fiber, and the like. Additionally grass crops, such as switch grass and the like have potential to be produced large-scale as another plant biomass source. For urban areas, the best potential plant biomass feedstock comprises yard waste (e.g., grass clippings, leaves, tree clippings, brush, etc.) and vegetable processing waste. Plant biomass is known to be the most prevalent form of carbohydrate available in nature and corn stover is the largest source of readily available plant biomass.

The term "pretreatment step" as used herein refers to any step intended to alter native biomass so that it can be more efficiently and economically converted to an alcohol, such as ethanol. Pretreatment methods can utilize acids of varying concentrations (including sulfuric acids, hydrochloric acids, organic acids, etc.) and/or other components such as ammonia, ammonium, lime, and the like. Pretreatment methods can additionally or alternatively utilize hydrothermal treatments including water, heat, steam or pressurized steam. Pretreatment can occur or be deployed in various types of containers, reactors, pipes, flow through cells and the like. Most pretreatment methods will cause hydrolysis of hemicellulose to pentose sugars. Conventional pretreatment methods do not hydrolyze lignin. Conventional pretreatment methods with acids alone also do not typically hydrolyze cellulose, although partial hydrolysis of cellulose may occur under some known pretreatment technologies. For example, the two-stage acid hydrolysis pretreatment process (FIG. 5) is known to hydrolyze a highly variable quantity of the cellulose portion, although the actual level of hydrolysis is dependent on many factors, including the type of biomass, conditions of the dilute acid pretreatment step, and so forth. The present invention provides for the novel use of ultrasonic energy as a pretreatment step, either alone or in combination with conventional pretreatment methods noted above. Unlike conventional methods, use of ultrasonic energy before, during and/or after a conventional pretreatment step or in place of a conventional pretreatment step is likely to cause additional hydrolysis of the various components, including significant hydrolysis of cellulose to glucose.

Biomass Conversion to Alcohol

Nearly all forms of ligno-cellulosic biomass, i.e., plant biomass, comprise three primary chemical fractions: hemicellulose, cellulose, and lignin. Hemicellulose is a polymer of short, highly-branched chains of mostly five-carbon pentose sugars (xylose and arabinose), and to a lesser extent six-carbon hexose sugars (galactose, glucose and mannose). These sugars are highly substituted with acetic acid. Because of its branched structure, hemicellulose is amorphous and relatively easy to hydrolyze (breakdown or cleave) to its individual constituent sugars by enzyme or dilute acid treatment. Cellulose is a linear polymer of glucose sugars, much like starch, which is the primary substrate of corn grain in dry grain and wet mill ethanol plants. However, unlike starch, the glucose sugars of cellulose are strung together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Lignin, which is a polymer of phenolic molecules, provides structural integrity to plants, and remains as residual material after the sugars in plant biomass have been fermented to ethanol. Lignin is a by-product of alcohol production and is considered a premium quality solid fuel because of its zero sulfur content and heating value, which is near that of sub-bituminous coal.

Typical ranges of hemicellulose, cellulose, and lignin concentrations in plants are presented in Table 1. See www.nrel.gov/biomass, National Renewable Energy Laboratory website. Cellulose makes up 30 to 50% of residues from agricultural, municipal, and forestry sources. While cellulose is more difficult to convert to ethanol than hemicellulose, it is the sugar polymers of hemicellulose which can be more readily hydrolyzed to their individual component sugars for subsequent fermentation to ethanol. Although hemicellulose sugars represent the "low-hanging" fruit for conversion to ethanol, the substantially higher content of cellulose represents the greater potential for maximizing alcohol yields, such as ethanol, on a per ton basis of plant biomass.

TABLE 1

Typical Levels of Cellulose, Hemicellulose and Lignin in Plant Biomass and Corn Stover

| Component | Plant Biomass Percent Dry Weight | Corn Stover Percent Dry Weight |
| --- | --- | --- |
| Cellulose | 30-50% | 38% |
| Hemicellulose | 20-40% | 32% |
| Lignin | 10-25% | 17% |

As noted above, the hemicellulose fraction of biomass contains hexose and pentose sugars, while the cellulose contains glucose. In current operations, only limited conversions are obtained. It is further known that of the sugars extracted, about 30 to 35% is xylose and about 35 to 40% is glucose (most all of which is currently converted only in post-pretreatment steps). Overall conversions, as well as over ethanol yields will vary depending on several factors such as biomass type, pretreatment type, and so forth.

Conventional methods used to convert biomass to alcohol include processes employing a concentrated acid hydrolysis pretreatment, a two-stage acid hydrolysis pretreatment as well as processes employing any known conventional pretreatment, such as hydrothermal or chemical pretreatments, followed by an enzymatic hydrolysis (i.e., enzyme-catalyzed hydrolysis) or simultaneous enzymatic hydrolysis and saccharification. Such pretreatment methods can include, but are not limited to, dilute acid hydrolysis, high pressure hot water-based methods, i.e., hydrothermal treatments such as steam explosion and aqueous hot water extraction, reactor systems (e.g., batch, continuous flow, counter-flow, flow-through, and the like), ammonia explosion, ammonia recycled percolation (ARP), lime treatment and a pH-based treatment.

Several of these methods generate nearly complete hydrolysis of the hemicellulose fraction to efficiently recover high yields of the soluble pentose sugars. This also facilitates the physical removal of the surrounding hemicellulose and lignin, thus exposing the cellulose to later processing. However, most, if not all, pretreatment approaches do not significantly hydrolyze the cellulose fraction of biomass.

Ultrasonic Technology

A transducer is a transducer having an active element made from a suitable material and means for generating a change in an external parameter, such as an electromagnetic field, which affects the active element. An ultrasonic transducer is capable of operating at frequencies in the ultrasonic range, typically considered at least about 17 kHz or above. For example, with active elements made from magnetostrictive materials, the element is changeable between a first shape in the absence of an electromagnetic field, and a second shape when in the presence of the electromagnetic field. In a similar manner, piezoelectric materials change shape in response to changes in voltage. Other materials are described in more detail below. In the example above, the transducer also includes means for providing an electrical signal to the components producing the electromagnetic field and an acoustic element, such as one or more horns, connected to the transducer for channeling energy to perform work.

Most ultrasonic transducers are capable of receiving up to about three (3) kW of electrical power and converting it into mechanical ultrasonic power at a frequency of about 20 kHz and in one embodiment this is the type of ultrasonic transducer used. (However, the invention is not limited to frequencies of 20 kHz and any suitable ultrasonic frequency required for the particular application can be used. And, as noted herein, in some instances it may be desirable to operate at less than ultrasonic frequencies, such as less than 17 kHz, down to about ten (10) kHz). A "high-powered" transducer is defined as any transducer capable of generating power in excess of three (3) kW. A "high-powered" transducer is typically capable of receiving up to 30 kW of electrical power and converting it into mechanical ultrasonic power at a frequency of at least about ten (10) kHz, typically about 20 kHz.

The active element in a transducer is typically made from a smart material, such as the magnetostrictive materials noted above. Smart materials are known to exhibit a change in shape in response to a change in input from an external parameter. Essentially, smart materials have the ability to "sense" their environment. Smart materials include magnetostrictive materials, such as ETREMA TERFENOL-D®, a metal alloy formed from the elements terbium, dysprosium and iron, fabricated by ETREMA Products, Inc. (hereinafter "Etrema"), in Ames, Iowa., under the brand name of "TERFENOL-D®." Other magnetostrictive materials useful herein include, but are not limited to, nickel, "Galfenol" (a gallium-iron alloy originally invented by the US Navy), ferrous metals, vandium permendur, metallic glass, and so forth. Smart materials also include materials such as ferroelectrics, electrostrictive materials including lead zirconate titanate or other ceramics, i.e., piezoceramics, and so forth. Electrostrictive materials change their shape when placed in an electrical field of varying voltage. This is known as the "piezoelectric" effect. Smart materials also include shape memory alloys.

External parameters which can be varied in order to cause the change in compliance to occur, include, but are not limited to, mass load, electrical load, prestress, and temperature, as well as ac and dc applied fields (or polarization fields), including electric, thermal and/or magnetic fields, as appropriate for different smart materials. For example, magnetostrictive materials such as TERFENOL-D®, are known to change shape in response to changes in (or application of) an applied magnetic field. Such variations in the magnetic field can be induced by providing a dc current to the motor or by varying the magnetic field strength. A magnetostrictive material can tolerate high mechanical stress, and has a relatively high energy density. High energy density enables more mechanical power output from more electrical power input and volume of smart material which thus reduces the size and weight of the transducer.

A giant magnetostrictive material can also be used for the active element. Examples of giant magnetostrictive materials include rare earth materials, rare earth-transition metal materials and compositions having rare earth materials, transition metals and other elements.

Ultrasonic energy, as with any sound wave, is essentially a series of compressions and rarefactions. When ultrasonic energy of sufficient intensity is applied to a liquid medium processing stream (through direct contact of the transducer with the liquid medium processing stream), cavitation of the medium and/or components contained in the medium typically occurs, as the medium can not react fast enough to accommodate the rapid movement of an ultrasonic horn. The energy that is elastically stored in the creation of the cavitation bubble is then released at a very localized level when the bubble collapses, thus generating very high temperatures, pressures, and sheering forces at the microscopic and even atomic levels. This transfer mechanism allows for the unique transfer and application of energy within a medium that can effect chemical and mechanical changes in that medium and/or the components therein. The extent of cavitation depends, in part, on the intensity of the ultrasonic energy applied.

EMBODIMENTS

As noted above, the various embodiments of the present invention provide for the insertion of ultrasonic energy into various points of the biomass to alcohol production process (through use of one or more ultrasonic transducers) to effect desired changes to the fluid medium and/or components flowing in the medium. Use of ultrasonic energy in this manner has multiple benefits, including, but not limited to, increasing the efficiency of biomass conversion, increasing the efficiency of alcohol production, improvement in and/or production of marketable by-products, and the like, as will be described in more detail herein.

FIG. 1 provides a simplified illustration of one embodiment of the present invention in which an ultrasonic transducer 100 having a horn 108 has been placed in a moving fluid medium 102 (of a biomass to alcohol process) containing large particulates 104. The moving fluid medium 102 may be moving at any suitable speed, such as about 189 to 1514 liters/min (about 50 to 400 gpm), although the invention is not so limited. Specific placement of the transducer 100 in the stream will vary depending upon the application. In some embodiments, a transducer having a cascade horn is used, which significantly increases the contact area with the fluid stream, thus enabling a higher contact volume per unit time. In other embodiments, a transducer having multiple horns is used. In some embodiments, multiple transducers are placed in parallel or series in the moving fluid medium 102.

In the embodiment shown in FIG. 1, ultrasonic energy 106 generated by the transducer 100 interacts directly with the moving fluid medium 102, causing the large particulates 104 to be broken down into small particulates 110 through cavitation, as described above. The small particulates 110 are all shown approximately the same size for simplification. In practice, the small particulates 110 may be a variety of sizes, including microscopic-sized.

The benefits of cavitation occurring in a biomass conversion stream are significant. For example, when used before, during and/or after a pretreatment step, cavitation of the moving fluid medium 102 and its large particulates 104 allows for destructuring, disaggregation, and disassociation of cellulose molecules from lignin components which would otherwise inhibit the hydrolization of cellulose prior to conversion to glucose. Ultrasonic cavitational forces are able to loosen, shake off and/or strip away cellulose molecules from lignin components. These forces are also able to destructure, disaggregate, decrystallize, soften, hydrate, and depolymerize the hemicellulose, cellulose and lignin. It is important to note, however, that overprocessing of the components, e.g., overprocessing of cellulose molecules prior to fermentation, may not be desirable. Specifically, if the applied sonication is too aggressive in terms of intensity, frequency and/or duration, it may be possible to cause some damage to the components being treated. Additionally, care must also be taken to not shear the biomass to the point that it is all converted into sugar too quickly, which could also inhibit or kill the yeast. Therefore, more intense sonication is limited to specific uses that may be considered less sensitive to this type of concern. This includes applications that do not require the starch or yeast to be present, such as when sonication is applied downstream of fermentation to kill contaminating recombinant fermentative microorganisms and to degrade, hydrolyze or denature transgenic nucleic acids present in the waste or product streams.

In some embodiments, particularly when high-powered ultrasonic energy is used, cavitation is likely occurring within the fluid medium itself. Cavitation of the fluid helps to enable the other changes taking place with the particulates. Specifically, disassociation of water molecules into hydrogen ions [H+] and hydroxyl groups [OH−] creates "free radicals, i.e., miniature "chemical reactors," which operate at a localized level to enable some of the benefits described herein, particularly those requiring greater "destruction" of the components, e.g., denaturing or degradation of transgenic proteins and transgenic nucleic acids of genetically modified feedstocks, rendering of bacteria and/or fingus and/or yeast as nonviable, and the like.

Figure 2:
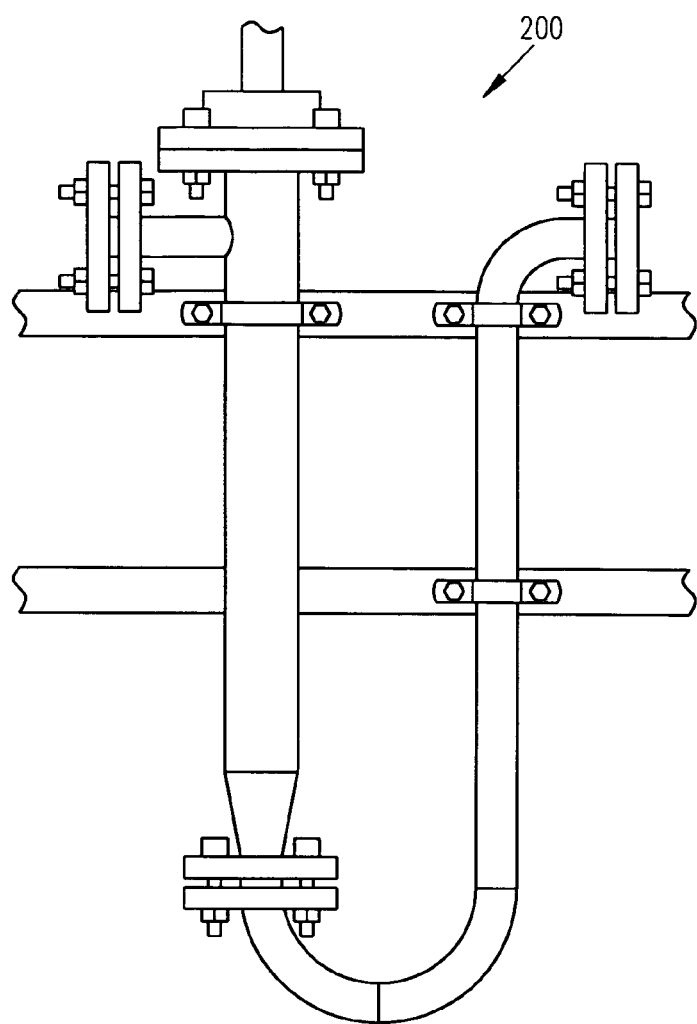
FIG. 2 is an illustration of an exemplary high-powered ultrasonic transducer with a cascade horn.
Figure 3:
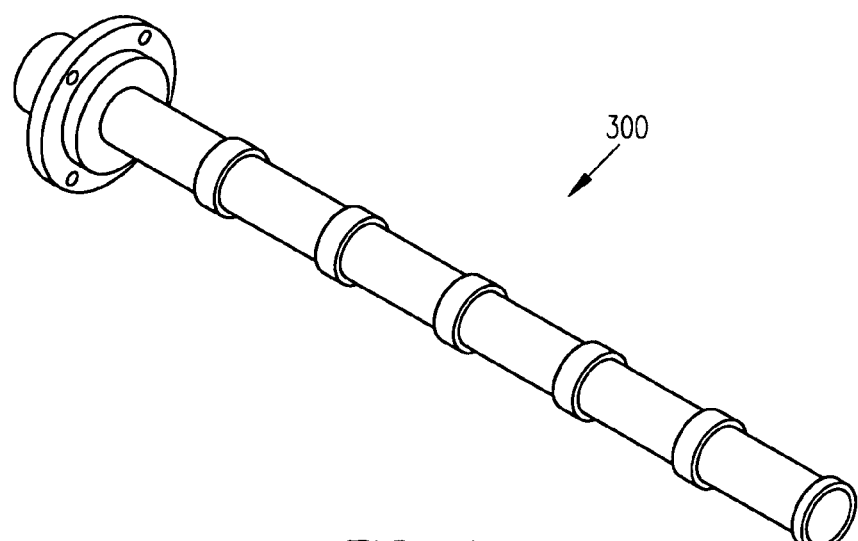
FIG. 3 is an illustration of a flow cell for use with the high-powered ultrasonic transducer of FIG. 2.

Examples of ultrasonic transducers that can be used in the present invention include, but are not limited to, the high-powered ultrasonic transducers described in U.S. Pat. No. 6,624,539, entitled, "High Powered Ultrasonic Transducers," by Hansen et al, which is incorporated herein by reference. Many of the high-powered transducers made by Dr. Heilscher GmbH in Teltow, Germany may also be useful herein. In another embodiment, a high-powered ultrasonic transducer having a cascade horn, such as the transducer 200 shown in FIG. 2 can be used. An exemplary flow cell designed for use with a cascade horn 300 is shown in FIG. 3. Although the flow cell shown in FIG. 3 has a U-shaped pipe, the invention is not so limited. The transducer, such as the transducer 200 shown in FIG. 2 can be inserted into a pipe of any dimension or geometry designed to force intimate contact between the horn and flow stream. In one embodiment, a Heilscher UIP 4000 Industrial Ultrasonic Processor is used.

High-powered transducers are particularly useful in embodiments in which transgenic proteins and transgenic nucleic acids of genetically modified recombinant fermentative microorganisms are being denatured or degraded, bacteria and/or fungus and/or yeast contaminants are being rendered nonviable, and so forth, although the invention is not so limited. Also, as noted above, the use of high-powered ultrasonic energy may not be the preferred embodiment in other applications, such as when the goal is to strip cellulose molecules from lignin components, for example. For these embodiments, it may be preferable to use a lower powered ultrasonic transducer. In addition to Heilscher GmbH, Branson Ultrasonics Corporation of Danbury, Connecticut also offers a variety of transducers, including immerscible transducers which use both magnetostrictive and piezoelectric materials which may be useful herein. In one embodiment, a piezoceramic transducer made by Branson Ultrasonics Corporation is used. In one embodiment, a 2000 Series Ultrasonic Assembly Transducer made by Branson Ultrasonics Corporation is used. Many of the transducers manufactured by Dukane Ultrasonics Inc. of St. Charles, Ill., may also be useful herein. In some embodiments, transducers having an exponential horn, step-stub horn, conical horn, Merkulov-horn or Fourier horn, and the like, can be used. It should be noted that the active element in the selected transducer can be any of the materials noted above in the discussion on ultrasonics.

Specific implementation parameters can easily be determined by adjusting the plumbing of an existing biomass to alcohol plant to accommodate an ultrasonic transducer system. For example, a special housing for the transducer can be added to the system. For a cascade horn, this is the U-shaped pipe 300 shown in FIG. 3 into which the transducer 200 of FIG. 2 is inserted and through which the fluid medium is directed. Additionally, the required level of ultrasonic energy and specific beneficial frequencies can be identified by measuring the conversion rates, e.g., speed of liquefaction or speed of fermentation, and intermediate or final product yields of the particular step of interest, while varying both power and frequency of the ultrasonic energy being applied.

Some of the benefits of creating cavitational forces at various locations in a biomass to alcohol production process include, but are not limited to, increased alcohol fermentation, decreased chemical and biological additives, reduction of energy costs (e.g., key processes such as cooking are completed at lower temperatures), denaturation or degradation of transgenic proteins and transgenic nucleic acids of genetically modified recombinant fermentative microorganisms and rendering nonviable bacteria and/or fungi and/or yeast contaminants. The benefit or benefits will vary depending on the type of biomass conversion pretreatment process being used. Achieving a particular benefit, however, is dependent on many factors, including where the ultrasonic energy, i.e., sonication, is applied in the process, the intensity and frequency at which sonication is applied, biomass content, biomass pretreatment process variables, and the like.

Figure 4:
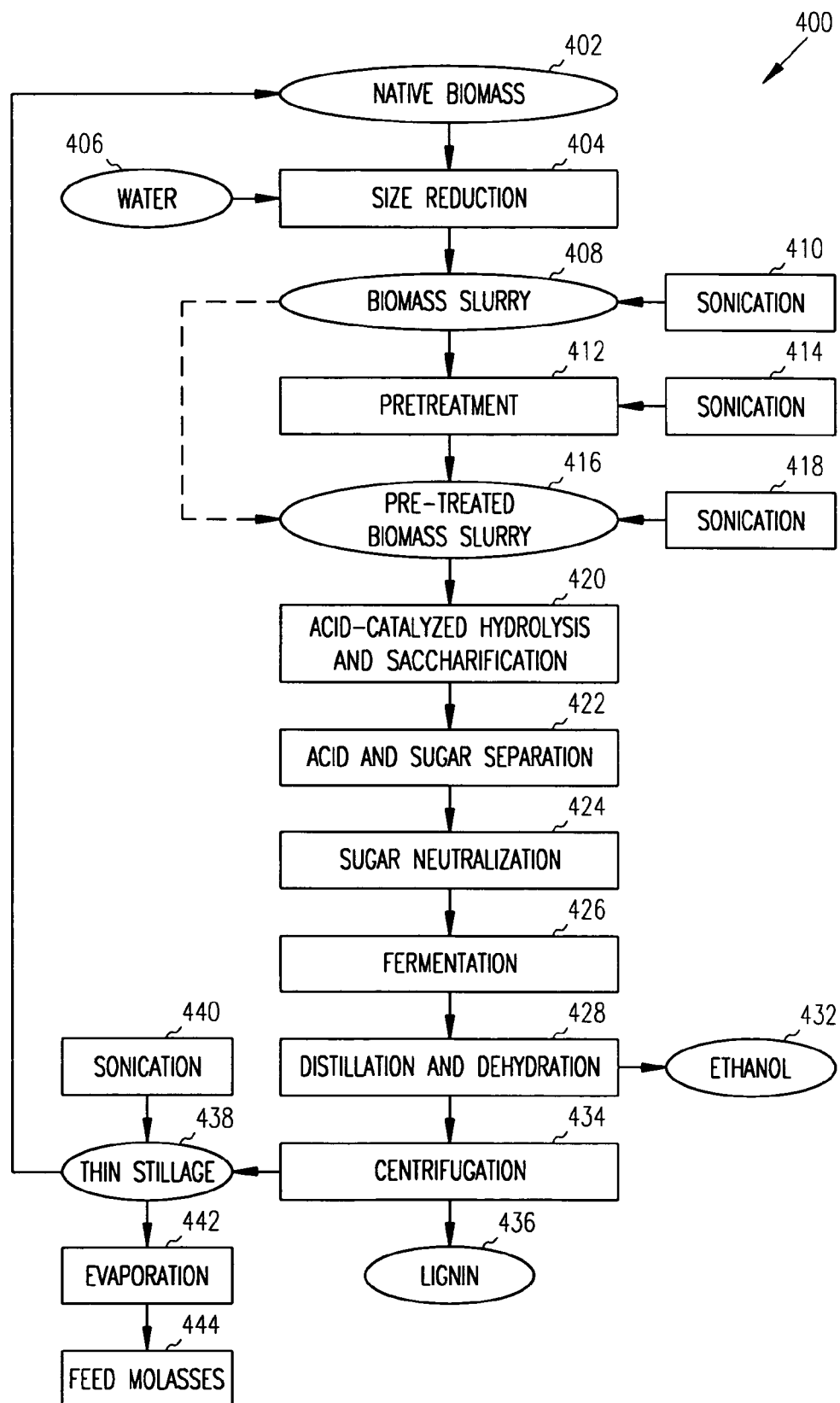
FIG. 4 is a diagram of a novel method of biomass to ethanol production using ultrasonic energy at various points in a process employing an ultrasonic concentrated acid hydrolysis pretreatment in embodiments of the present invention.
Figure 5:
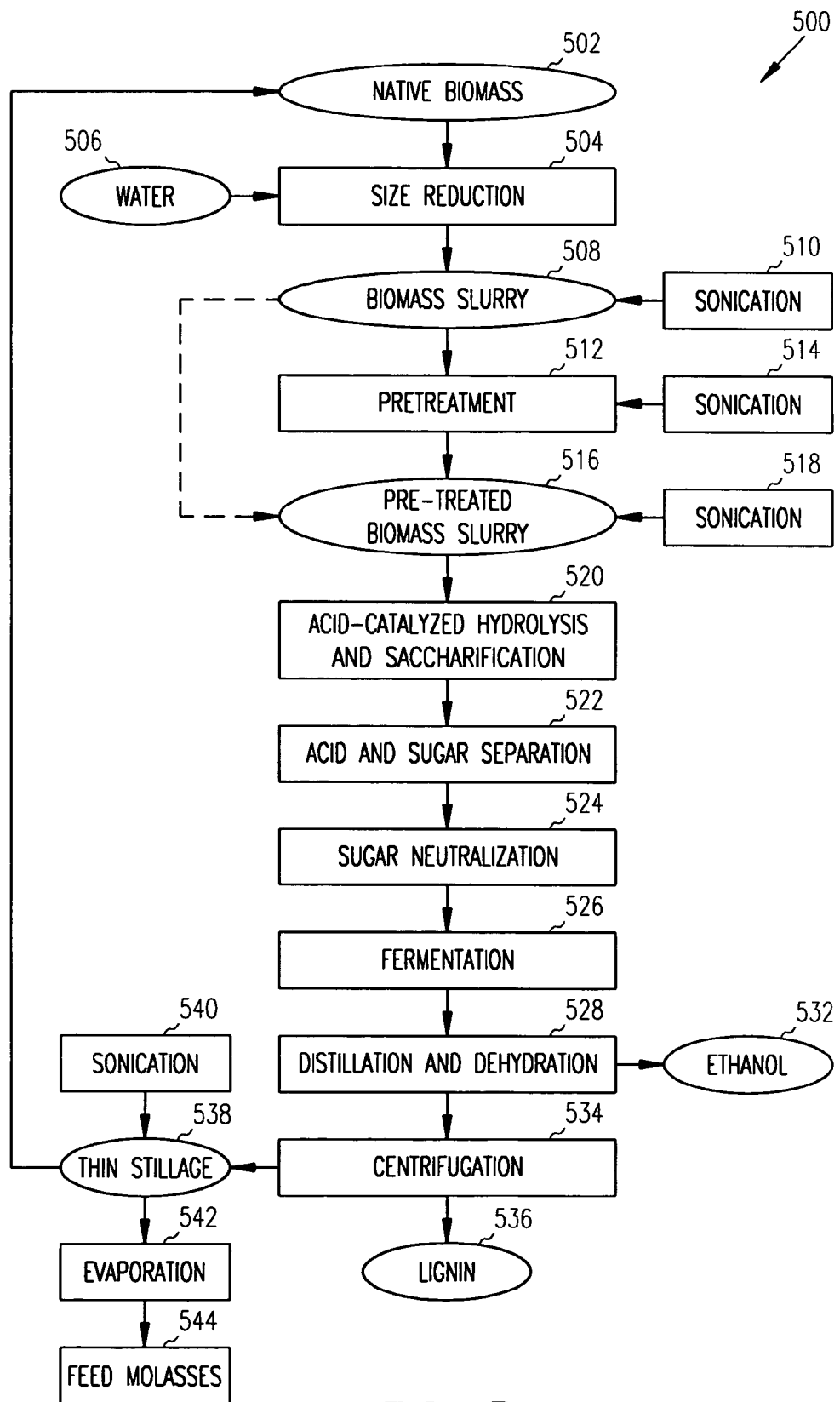
FIG. 5 is a diagram of a novel method of biomass to ethanol production using ultrasonic energy at various points in a process employing a two stage acid hydrolysis pretreatment in embodiments of the present invention.
Figure 6:
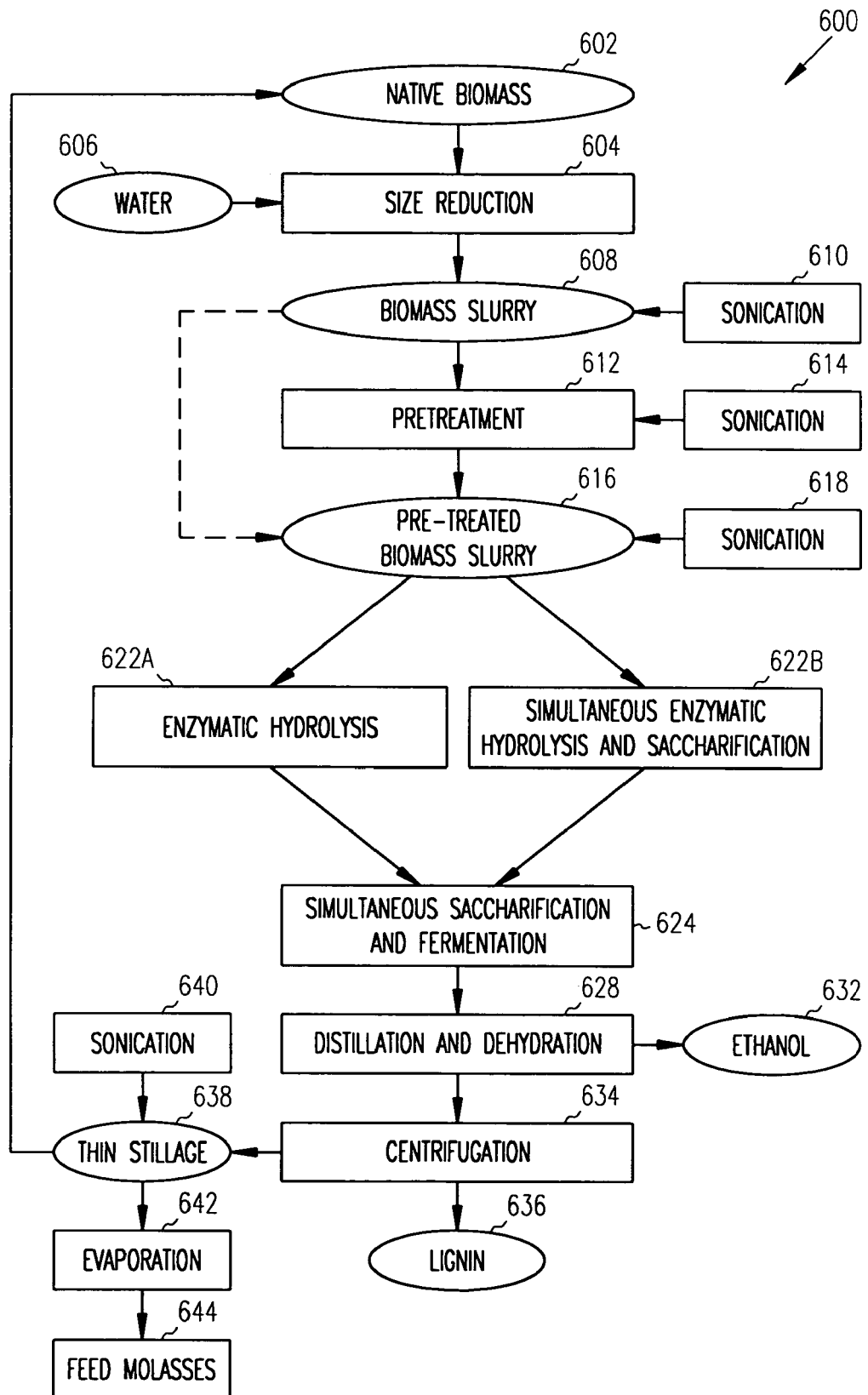
FIG. 6 is a diagram of a novel method of biomass to ethanol production using ultrasonic energy at various points in a process employing a hydrothermal or chemical pretreatment followed by enzymatic hydrolysis or simultaneous enzymatic hydrolysis and saccharification in embodiments of the present invention.

FIGS. 4-6 are flow diagrams illustrating novel methods for converting native biomass to ethanol in three different processes by including one or more sonication steps in various locations, although the invention is not so limited. See http://www.nrel.gov/biomass, supra, and http://www.ott.doe.gov/biofuels for additional details. Again, sonication applied as described herein is also useful in other grain-based alcohol production facilities as well as in other types of biomass to alcohol processes (described below). In one embodiment, ultrasonic energy is utilized only once during the process in just one location. In other embodiments, sonication is utilized in more than one location with multiple transducers to increase and/or vary the benefits obtained.

In one embodiment, at least one of the one or more transducers is a high-powered transducer generating about three (3) to ten (10) kW. In one embodiment, the high-powered transducer operates at a frequency of about ten (10) to 20 kHz. In one embodiment, the high-powered transducer is a high-powered ultrasonic transducer operating at a frequency of at least about 17 kHz. In one embodiment, the frequency is about 19.5 to 20.5 kHz. In one embodiment each of the one or more transducers operate for no more than about ten minutes in the moving fluid medium 102, although the invention is not so limited and the transducers can operate for any suitable amount of time as needed. In one embodiment, multiple transducers operate for less than five (5) minutes to achieve the desired result. In one embodiment, about three (3) to ten (10) kW of power is used in one or more transducers at a frequency of between about ten (10) and 20 kHz for greater than zero (0) minutes up to about ten (10) minutes.

It is important to use adequate power for the particular application as otherwise the cavitational forces transmitted will not be sufficient. This is particularly true for mediums known to have a relatively high solids content, such as about 20 to 40% by weight. In such instances, it is likely at least three (3) kW of power may be needed. In other embodiments, much higher powered transducers can be used, such as greater than three (3) kW up to about ten (10) kW.

FIG. 4 is a diagram of a novel method of biomass to ethanol production using ultrasonic energy at various points in a process 400 utilizing a concentrated acid hydrolysis pretreatment. In this embodiment, native biomass 402, such as lignocellulosic biomass, is subjected to a size reduction step 404. Typically, the native biomass 402 is passed through shredders to reduce to a suitable size, as is known in the art. Addition of a suitable amount of water to the shredded biomass produces a biomass slurry 408. In one embodiment, the biomass slurry 408 is subjected to sonication 410 to cause cavitation that hydrolyzes at least a portion of the cellulose and hemicellulose. In some embodiments, as shown in FIG. 4, the sonication 410 applied at this point in the process essentially replaces the conventional pretreatment step 412 (discussed below) and the sonicated slurry, which is now a "pretreated biomass slurry" 416, is then subjected to the next step, which in this instance is an acid-catalyzed hydrolysis and saccharification 420, but in other embodiments is an enzyme-catalyzed hydrolysis or simultaneous enzyme-catalyzed hydrolysis and saccharification step (See FIG. 6).

Assuming the pretreatment step 412 is utilized, the biomass slurry 408 (which may or may not have been subjected to sonication 410) then undergoes the pretreatment step 412 which essentially enables subsequent fermentation by hydrolyzing the hemicellulose fraction. In a concentrated acid hydrolysis pretreatment step 412, acid is added in a concentration and manner sufficient to hydrolyze the hemicellulose fraction and decrystallize the cellulose into an amorphous state. In most embodiments concentrated sulfuric acid is used.

In one embodiment, sonication 414 is additionally or alternatively used during the pretreatment step 412 to again cause cavitation that allows at least a portion of the cellulose to be hydrolyzed (and hemicellulose to be further hydrolyzed) during this step 412. The pretreatment step 412 produces a pretreated biomass slurry 416 which can additionally or alternatively be subjected to sonication 418 to further enhance hydrolyzation of the components.

The pre-treated biomass slurry 416 then undergoes an acid-catalyzed hydrolysis and saccharification step 420 through addition of a diluted acid in a concentration sufficient to cause at least a portion of the cellulose to hydrolyze. The specifics as to concentration, temperatures, amounts and duration will vary depending on several factors, including the type of biomass being used, costs, desired results, and the like. In most embodiments, dilute sulfuric acid is used.

As a result, the hemicellulose and cellulose are hydrolyzed to fermentable sugars, although the acid and sugars must first be separated in an acid and sugar separation step 422 understood by those skilled in the art. This is followed by a sugar neutralization step 424 also understood by those skilled in the art. After neutralization, the sugars are fermented in a fermentation step 426 in which genetically engineered yeast or bacteria is added to convert both glucose and pentose sugars (xylose) to ethanol and $CO_2$. Yeast can optionally be recycled in a yeast recycling step. It is important to note that it is not desirable to utilize sonication during the fermentation step 426 since it will kill fermentative microorganisms (yeast or bacteria) being utilized in this step to produce the alcohol.

Subsequent to the fermentation step 426 is a distillation and dehydration step 428 in which the fermented sugars are pumped into distillation columns where they are boiled to vaporize the ethanol. The ethanol vapor is condensed in the distillation columns, and liquid ethanol exits the top of the distillation columns at about 95% purity (190 proof). The "190-proof" ethanol then goes through a molecular sieve dehydration column, which removes the remaining residual water from the ethanol, to yield a final product of essentially 100% ethanol (199.5% proof). This anhydrous ethanol is now ready for to be used as fuel.

Finally, a centrifugation step 434 involves centrifuging the residuals produced with the distillation and dehydration step 428, i.e., "whole stillage" in order to separate the insoluble solids or wet cake, i.e., lignin 436, from the liquid or thin stillage 438. The lignin 436 is typically used as a boiler fuel.

In one embodiment, the thin stillage 438 is additionally or alternatively subjected to sonication 440 to kill the fermentative recombinant microorganisms and degrade, depolymerize and/or denature any transgenic nucleic acids present. The thin stillage 438 enters evaporators in an evaporation step 442 in order to boil away moisture, leaving a thick syrup or feed molasses 444. In some embodiments, at least a portion of the thin stillage 438 is recycled for use again in the system.

FIG. 5 is a diagram of a novel method of biomass to ethanol production using ultrasonic energy at various points in a process 500 utilizing a two-stage acid hydrolysis pretreatment method. In this process native biomass 502 is subjected to the same initial steps described in FIG. 4 including size reduction 504 and addition of water 506 to form a biomass slurry 508. Again, the biomass slurry 508 can be subjected to sonication 510 to cause cavitation that hydrolyzes at least a portion of the cellulose and hemicellulose. In some embodiments, as shown in FIG. 5, the sonication 510 applied at this point in the process essentially replaces the conventional pretreatment step 512 and the sonicated slurry, which is now a "pretreated biomass slurry" 516, is then subjected to the next step, which in this instance is an acid-catalyzed hydrolysis and saccharification 520, but in other embodiments is an enzymatic hydrolysis or a simultaneous enzymatic hydrolysis and saccharification. (See FIG. 6). (This embodiment is essentially the same embodiment as shown in FIG. 4 when the conventional pretreatment step 412 is omitted).

Assuming the pretreatment step 512 is utilized, the biomass slurry 508 (which may more may not have been subjected to sonication 510) then undergoes the pretreatment step 512, which essentially enables subsequent fermentation by hydrolyzing the hemicellulose fraction, and, in this instance, a small or partial portion of the cellulose fraction. In a two-stage acid hydrolysis pretreatment step 512 dilute acid is added in a suitable manner, concentration and amount together with heat in a suitable amount for a suitable period of time to hydrolyze the hemicellulose in a first step. This is followed by a second step in which more concentrated acid, such as sulfuric acid, is added to attempt to achieve hydrolyzation of at least a portion of the cellulose fraction.

In one embodiment, sonication 514 is additionally or alternatively used during either or both of the stages of the pretreatment step 512 to again cause cavitation that allows at least a portion of the cellulose to be hydrolyzed (and hemicellulose to be further hydrolyzed) during this step 512. The pretreatment step 512 produces a pre-treated biomass slurry 516 which can additionally or alternatively be subjected to additional sonication 518 to further enhance hydrolyzation of the components.

As compared with the process 400 described in FIG. 4, it is thought that the pretreatment step 512 in the process 500 of FIG. 5 increases sugar yields from both cellulose and hemicellulose fractions. Sonication applied before and/or during pretreatment 512 improves the hydrolysis of both the cellulose and hemicellulose significantly, thus increasing the ethanol yield during fermentation.

The pretreated biomass slurry 516 then undergoes an acid catalyzed cellulose hydrolysis and saccharification step 520 as described in FIG. 4. The resulting sugars are separated from the acid in an acid and sugar separation step 524, followed by sugar neutralization 524 and so forth, followed by fermentation 526 and distillation and dehydration 528 to produce ethanol 532 as described in FIG. 4. Again, it is not desirable to utilize sonication during fermentation 526 for the reasons stated herein.

Finally, a centrifugation step 534 involves centrifuging the residuals produced with the distillation and dehydration step 528 to separate the lignin 536 from the liquid or thin stillage 538. In one embodiment, the thin stillage 538 is additionally or alternatively subjected to sonication 540 to kill the fermentative recombinant microorganisms and degrade, depolymerize and/or denature any transgenic nucleic acids present. The thin stillage 538 enters evaporators in an evaporation step 542 in order to boil away moisture, leaving a thick syrup or feed molasses 544. In some embodiments, at least a portion of the thin stillage 538 is recycled for use again in the system.

FIG. 6 is a diagram of a novel method of biomass to ethanol production using ultrasonic energy at various points in a process 600 utilizing a hydrothermal or chemical pretreatment method followed by enzymatic hydrolysis or simultaneous enzymatic hydrolysis and saccharification. In this process native biomass 602 is subjected to the same initial steps described in FIG. 4 including size reduction 604 and addition of water 606 to form a biomass slurry 608. Again, the biomass slurry 608 can be subjected to sonication 610 to cause cavitation that hydrolyzes at least a portion of the cellulose and hemicellulose. In some embodiments, as shown in FIG. 6, the sonication 610 applied at this point in the process essentially replaces the conventional pretreatment step 612 and the sonicated slurry, which is essentially a "pretreated biomass slurry" 616, is then subjected to the next step, which in this instance can be an enzymatic hydrolysis step 622A or a simultaneous enzymatic hydrolysis and saccharification step 622B, depending on the type of enzyme used.

Assuming the pretreatment step 612 is utilized, the biomass slurry 608 (which may more may not have been subjected to sonication 610) then undergoes the pretreatment step 612, which essentially enables subsequent fermentation by hydrolyzing the hemicellulose fraction. The pretreatment step 612 in this particular embodiment involves the use of hydrothermal (pressurized steam or hot water) or chemicals (dilute acid, ammonia, etc.), although the invention is not so limited. Virtually any type of pretreatment can be used prior to steps 622A or 622B. The pretreatment step 612 is intended to cause the hemicellulose to hydrolyze, i.e., be converted to pentose sugars, and the cellulose to be decrystallized into an amorphous state.

In one embodiment, sonication 614 is additionally or alternatively used during the pretreatment step 612 to again cause cavitation that allows at least a portion of the cellulose to be hydrolyzed (and hemicellulose to be further hydrolyzed) during this step 612. The pretreatment step 612 produces a pre-treated biomass slurry 616 which can additionally or alternatively be subjected to additional sonication 618 to further enhance hydrolyzation of the components.

The pretreated biomass slurry 616 then undergoes either an enzymatic hydrolysis step 622A or a simultaneous enzymatic hydrolysis and saccharification step 622B to convert at least a portion of the cellulose to glucose sugars. Either enzymatic hydrolysis or simultaneous enzymatic hydrolysis and saccharification are preferred over the acid hydrolysis steps described in FIGS. 4 and 5 because they provide many benefits, including an increased conversion rate, lower capital cost (non-corrosive environment) reduced chemical costs and elimination of chemical waste disposal.

A simultaneous saccharification and fermentation step 624 is next, which uses genetically-modified yeast or bacterial strains that can utilize both pentose and glucose sugars. Again, sonication is not recommended during the fermentation step 624 for the reasons stated herein. This is followed by the distillation and dehydration step 628 to produce ethanol 632 as described above.

Finally, a centrifugation step 634 involves centrifuging the residuals produced with the distillation and dehydration step 628 to separate the lignin 636 from the liquid or thin stillage 638. In one embodiment, the thin stillage 638 is additionally or alternatively subjected to sonication 640 to kill the fermentative microorganisms and degrade, depolymerize and/or denature any transgenic nucleic acids present. The thin stillage 638 enters evaporators in an evaporation step 642 in order to boil away moisture, leaving a thick syrup or feed molasses 644. In some embodiments, at least a portion of the thin stillage 638 is recycled for use again in the system.

Pretreatment is the most expensive step in the operational cost of biomass to alcohol production. Utilization of the system and methods of the present invention help to reduce various pretreatment costs. This includes, but is not limited to, reduction in amount of biomass milling or grinding required, lower capital cost construction, elimination or reduction of acid addition and/or other process chemicals, elimination of need for corrosive resistant equipment, reduced water requirement, reduced heat (energy) requirement, elimination or reduction of gypsum disposal (resulting from acid use), achievement of high pentose sugar recovery, production of a hemicellulose and cellulose hydrolysate with a minimal inhibitory effect on fermentation, and the like.

The novel system and methods described herein are expected to increase overall yields of alcohol, such as ethanol, by at least 10% up to 100% or more. Glucose yields will also increase by at least 10% up to 100% or more. Yields of other sugars are also expected to increase. Actual yields are dependent on many factors including, but not limited to, type of biomass feedstock being used, type of pretreatment methods being employed, and so forth. Additionally, when used after fermentation, sonication can also significantly decrease the presence of unwanted genetically engineered materials in product and waste streams, such as the feed molasses stream, in some instances reducing these levels to near zero percent.

Although the power and intensity levels of the sonication required will vary depending on the particular application, it is understood by those skilled in the art that the level of ultrasonic agitation needed in the present invention must be greater than a level which, at most, is capable only of converting the components in the biomass slurry into microcrystalline particles, such as cellulose into microcrystalline cellulose. Specifically, the level of sonication agitation utilized must go beyond inducing microcrystallization and further cause at least some hydrolyzation of the components. Transducer variables which can be adjusted to accomplish the desired results include, but are not limited to, power, intensity, duration, type, location in the flow stream, and so forth.

However, it is undesirable to overprocess the components, including cellulose, particularly prior to fermentation. Testing can be performed to determine the most beneficial location, duration, intensity and frequency for sonication in and around the pretreatment step. In some instances, a combination of sonication both before, after, and during pretreatment can be used. Again, it is also possible that the application of ultrasonic energy to the biomass slurry may allow the conventional pretreatment step to be eliminated altogether.

Other biomass to alcohol technologies in which ultrasonication can be used are discussed below. Although these processes are discussed in general terms, it is to be understood that most of these processes are currently under development and may vary somewhat in their final commercial form. However, those skilled in the art will understand that the use of ultrasonication before, during and/or after the pretreatment process can achieve the various benefits described herein. Additionally, application of ultrasonication after fermentation, such as to the thin stillage, will provide additional benefits as described herein.

Dilute Sulfuric Acid Process. Addition of dilute sulfuric acid to plant biomass is often favored because of the potential for high yields of sugars possible from both the hemicellulose fraction during pretreatment and from the remaining cellulose in subsequent enzymatic processing. However, pretreatment by this approach is currently the single most expensive step in bioprocessing for production of ethanol from plant biomass, and no other approach has been established to be significantly lower in costs.

Such processes have less than optimal yields of glucose conversion from cellulose. With the dilute acid treatment process, it is believed that cooling in the presence of the pretreated solids results in re-precipitation of solubilized lignin upon the pretreated solids, negatively affecting subsequent enzymatic hydrolysis by cellulase enzymes.

In one embodiment, ultrasonication is applied before, during and/or after pretreatment in a dilute sulfuric acid process and/or after fermentation, typically to the thin stillage component. It is expected that alcohol yields will increase significantly through application of ultrasonication as described herein. It is also expected that other benefits as described herein will occur.

Aqueous Hot Wash Extraction Process. This method is a variation of a dilute acid pretreatment, and may also be applicable to other pretreatment processes. An aqueous hot wash extraction process involves a high temperature separation and pressurized hot water washing (e.g., about 135° C.) of the pretreated solids that allows for separation of lignin that was solubilized during pretreatment. Such a processing step prevents re-precipitation of lignin and/or xylan (hemicellulose oligomers), originally solubilized under pretreatment conditions, back upon the pretreated cellulosic solids. Compared to traditional dilute acid pretreatment, the hot separation and washing technique improves lignin solubilization by as much as three fold, and dramatically enhances the speed of cellulose hydrolysis and ethanol production.

In one embodiment, ultrasonication is applied before, during and/or after pretreatment in a dilute sulfuric acid process and/or after fermentation, typically to the thin stillage component. It is expected that alcohol yields will increase significantly and associated production costs will decrease through application of ultrasonication as described herein. It is also expected that other benefits as described herein will occur.

Flow-Through Reactor Process. As a version of an aqueous hot wash extraction process, flow-through reactors pass hot water through a stationary bed of cellulosic plant biomass with or without dilute sulfuric acid addition. The process hydrolyzes hemicellulose to nearly theoretical yields of monomeric sugars, removes lignin, and produces highly digestible cellulose that can achieve high glucose yields with low cellulase loadings. Flow-through reactors have several advantages for plant biomass pretreatment including virtual elimination of the need for chemicals during both pretreatment and pre-fermentation conditioning, high yields of hemicellulose sugars, production of highly digestible cellulose, and a less corrosive environment from no acid addition. These advantages translate to potential reduction in capital construction and chemical costs. However, flow-through reactors require high water consumption, high energy use, and a complex configuration, which present commercial challenges.

In one embodiment, ultrasonication is applied before, during and/or after pretreatment in a flow-through reactor process and/or after fermentation, typically to the thin stillage component. It is expected that alcohol yields will increase significantly and associated production costs will decrease through application of ultrasonication as described herein. It is also expected that other benefits as described herein will occur.

Steam Explosion Process. Also referred to as autohydrolysis, steam explosion is one of the most cost-effective methods of pretreatment currently known for ligno-cellulosic plant biomass. The steam explosion process usually occurs in a batch reactor in which chipped or shredded plant biomass is treated with high pressure or saturated steam (160-260° C.) for a short period of time followed by a rapid reduction in pressure creating a flash decompression. The steam conditions initiate autohydrolysis reactions in which weak acids from the deacetylation of hemicellulose act as catalysts in the hydrolysis of hemicellulose. The treatment also creates a physical disaggregation and rupture of the ligno-cellulosic fibers, separation of cellulose and lignin polymeric components, and depolymerization of lignin to phenolic compounds. Factors that affect steam explosion efficacy are residence time, which can vary from a few seconds to several minutes, temperature, plant biomass particle or chip size, and moisture content.

One advantage to steam explosion is that it provides a cellulose substrate suitable for enzymatic hydrolysis. However, some ligno-cellulosic materials are particularly resistant to steam explosion, and higher steam temperatures are required to overcome this drawback. Alternatively, impregnation of chemicals, primarily $SO_2$ or sulphuric acid, can effectively improve enzymatic hydrolysis and decrease the production of inhibitory compounds. As an example, maximum sugar yields following enzymatic hydrolysis have been recovered from corn fiber steam exploded at 190° C. for 5 minutes with 6% $SO_2$.

The main drawbacks to steam explosion are the formation of various toxic compounds inhibitory to microbial fermentation, and low pentose sugar recovery in undegraded form. Although the nature and concentrations of the final inhibiting compounds vary greatly with pretreatment conditions and the raw material used, the inhibitors produced during steam explosion belong to three major groups: weak acids from deacetylation of hemicellulose and breakdown of lignin, furans (furfural) from sugar degradation, and phenolic compounds from lignin degradation. Nevertheless, steam explosion is effective at large particle size, giving the advantages of elimination or reduction of milling, lower costs for materials of construction, lower costs for process chemicals, and eliminated gypsum disposal derived from the elimination of acid addition, all of which are considered highly attractive enough for further research to optimize the process for commercialization.

In one embodiment, ultrasonication is applied before, during and/or after pretreatment in a steam explosion process and/or after fermentation, typically to the thin stillage component. It is expected that alcohol yields will increase significantly through application of ultrasonication as described herein. It is also expected that other benefits as described herein will occur.

Ammonia Recycled Percolation (ARP). ARP is a pretreatment method that utilizes aqueous ammonia in a recycle mode. ARP achieves high degree of lignin removal while keeping cellulose content intact. In order to prevent the loss of hemicellulose along with lignin during delignification, two stage processes have been devised in which water or dilute-acid percolation process and the ARP are operated in succession. The solid fraction which remains is mainly cellulose. The fractionation of hemicellulose, lignin, and cellulose improves the overall plant biomass-to-ethanol conversion process since each of the plant biomass constituents can be individually utilized more efficiently.

Lime Treatment. Treatment of lignocellulosic plant biomass with lime enhances cellulose digestibility by cellulase enzymes or cellulolytic microorganisms (the bacteria or molds which produce the cellulase enzymes used for enzymatic hydrolysis). Lime enhances digestibility by removing lignin as well as acetyl groups from hemicellulose. Lime has several pretreatment advantages: 1) it is a low cost alkali, 2) it is safe to handle, 3) processing conditions are relatively mild, and 4) it is effective.

In one embodiment, ultrasonication is applied before, during and/or after pretreatment in an ARP process and/or after fermentation, typically to the thin stillage component. It is expected that alcohol yields will increase significantly through application of ultrasonication as described herein. It is also expected that other benefits as described herein will occur.

The benefits of sonication applied to the appropriate location or locations in a biomass to alcohol process, such as a plant biomass to ethanol process are many:

In one embodiment, ultrasonic energy is used for the pretreatment of ligno-cellulosic plant biomass in which pretreated plant biomass is subsequently converted to ethanol via fermentation.

In one embodiment, ultrasonic energy is used for the pretreatment of ligno-cellulosic plant biomass in which pretreated plant biomass is subsequently converted to monomeric pentose and hexose sugars.

In one embodiment, ultrasonic energy is used for the pretreatment of ligno-cellulosic plant biomass which effectively creates destructuring, disaggregation, decrystallization, softening, hydration, depolymerization, and hydrolysis of hemicellulose, cellulose, and lignin of said ligno-cellulosic plant biomass.

In one embodiment, ultrasonic energy is used for the pretreatment of ligno-cellulosic plant biomass in order to produce more highly digestible cellulose for subsequent enzymatic or chemical hydrolysis to glucose.

In one embodiment, an ultrasonication process is provided for the pretreatment of ligno-cellulosic plant biomass for ethanol production comprising any or all of the following pretreatment conditions: suspension of said ligno-cellulosic plant biomass material in an aqueous medium with any level of percent total dissolved solids and percent total suspended solids; addition of chemicals including, but not limited to, acid, base, ammonia, and sulfur dioxide; the addition of heat or pressurized steam ranging anywhere from 0° C. to 300° C. for an unlimited amount of residence time; a rapid reduction in pressure creating a flash decompression; application of ultrasonication (provide range of watts/range of frequency, etc.) for an unlimited amount of time; a batch reactor system, a continuous flow system, a counter-current (counter-flow) system, or a flow-through reactor system. In one embodiment, an ultrasonication process is used in conjunction with, i.e., interfaced with an existing ligno-cellulosic plant biomass pretreatment technologies for the production of monomeric pentose and hexose sugars and the production of ethanol, in which said pretreatment technologies include, but are not limited to, dilute acid hydrolysis, steam explosion, ammonia explosion, aqueous ammonia recycled percolation, lime treatment, steam explosion, aqueous hot water extraction, any other high pressure hot water based methods (hydrothermal treatments), batch reactor systems, continuous flow systems, counter-current (counter-flow) systems, or flow-through reactor systems.

In one embodiment, an ultrasonication process is used that enables or improves process efficiencies, process economics, process design, and commercial scale-up, when used in conjunction with, i.e., interfaced with existing ligno-cellulosic plant biomass pretreatment technologies for the pretreatment processes described herein, in which any of the following factors, conditions, or steps are enabled or improved: production of highly digestible cellulose solids that can achieve high glucose yields with lower cellulase enzyme loadings, resulting in lower cellulase costs; elimination of the need for chemicals during both pretreatment and pre-fermentation conditioning, i.e., elimination of the need for acid during pretreatment; lower the cost of materials of construction because of a less corrosive environment; reduction in heat and energy demand; reduction in water usage; minimization or elimination of the formation of degraded sugars and subsequent formation of chemicals such as furfural that inhibit microbial fermentation, primarily due to reducing heat requirements and elimination of chemical requirements; and optimization of pretreatment process settings in flowrate, temperature, pressure, and chemical (acid) level to maximize hemicellulose recovery, lignin removal, and cellulose digestibility by enzymes or chemical treatment.

In one embodiment, an ultrasonication process is used that enables or improves process efficiencies, process economics, process design, and commercial scale-up factors listed above, when used in conjunction with, interfaced with either before of after, or integrated within any of the following plant biomass-to-ethanol processes: concentrated acid hydrolysis, two-stage dilute acid hydrolysis and enzymatic hydrolysis.

In one embodiment, ultrasonic energy is used to specifically improve the yield of ethanol production, or the rate (speed) of ethanol production, or the combination of the yield of ethanol and rate (speed) of ethanol production, in any commercial plant biomass-to-ethanol process.

In one embodiment, ultrasonic energy is applied to any point or processing step prior to (upstream to) fermentation in order to kill any contaminating microorganisms, including bacteria, fungi, and yeast, which reduces the possibility of microbial contamination during the fermentation stage.

In one embodiment, ultrasonic energy is applied to any point or processing step subsequent to (downstream from) fermentation in order to kill any genetically enhanced, recombinant fermentative microorganisms, including fermentative bacteria, fungi, and yeast.

In one embodiment, ultrasonic energy is applied at any point or processing step in any plant biomass-to-ethanol process in order to degrade, depolymerize, or denature transgenic DNA or transgenic RNA derived from any transgenic/recombinant fermentative microorganism, in any food or feed processing product, and in waste water streams, such that said transgene DNA or RNA, or portion of transgene DNA or RNA, can not be detected by DNA and RNA molecular detection methods.

In one embodiment ultrasonic energy is applied at any point after fermentation in any plant biomass-to-ethanol process in order to degrade or denature transgenic protein derived from any transgenic/recombinant fermentative microorganism, in any food or feed processing product, and in waste water streams, such that said transgenic protein can not be detected by immunological detection methods.

Embodiments of the present invention will now be further described in the following non-limiting example.

EXAMPLE

Introduction

The application of ultrasonic energy was evaluated for various biomass feedstocks for the biomass-to-ethanol process. The objective of the biomass studies was to determine if ultrasonic energy could function as a pretreatment methodology for ethanol production. In doing so, ultrasonic energy would be evaluated for its ability to decrystallize cellulose such that it becomes more digestible by cellulase enzymes. This process would rely upon ultrasonic energy to swell and hydrate crystalline cellulose, and essentially decrystallize it, in order to make cellulose highly digestible. The impact of the ultrasonic energy treatment on the efficiency of cellulose hydrolysis was measured by the levels of glucose released, and the levels of ethanol produced in subsequent fermentations.

Biomass-to-Ethanol Studies

Two batch process ultrasonic energy studies were carried out at the ETREMA Products, Inc. facility in Ames, Iowa. The biomass feedstock substrates evaluated for conversion to ethanol were ground switch grass from a South Dakota field, and purified crystalline cellulose ("Sigmacell® Cellulose") from Sigma-Aldrich Company, having offices in St. Louis, Mo. The open, batch sonication process was deployed using a hammer-head style horn, and with 500 mL liquid slurry samples sonicated within 1000 mL glass beakers. For the biomass feedstocks, all sonications were carried out at a power of about two (2) kW and a frequency of about 20 kHz, with residence times ranging from zero (0) to about 15 minutes. Sonicated biomass samples were then transferred to sterile plastic containers and held at room temperature. Immediately following the application of ultrasonic energy, laboratory cellulase enzyme treatments and fermentations were carried out. Glucose sugars were quantitated by High Performance Liquid Chromatography (HPLC), and ethanol yield was measured by Gas Chromatography (GC).

Study 1

Figure 7:
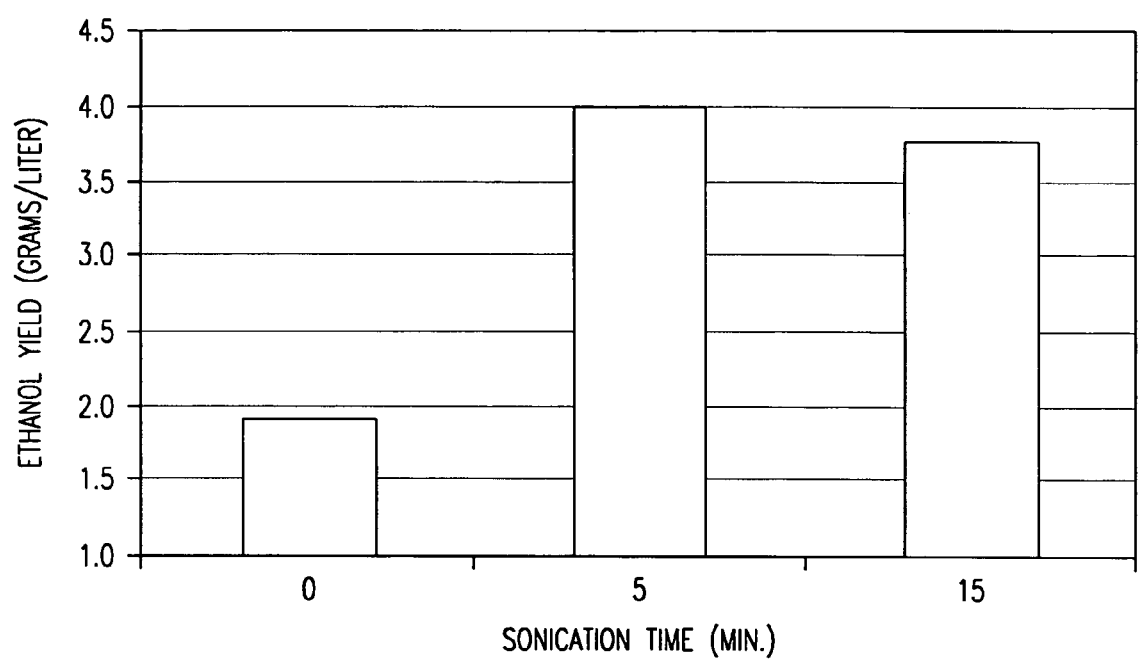
FIG. 7 is a graph showing ethanol yield versus sonication time for sonication of switch grass slurry and impact on ethanol fermentation in embodiments of the present invention.

The first study deployed ultrasonic energy in a batch process without the addition of any chemicals. Finely ground switch grass was suspended at about 10% w/v (weight/volume) solids in deionized water. Three independent slurry suspensions were made in which the final volume for each suspension was 500 mL. Sonications were carried out for zero (0) minutes (control), about 5 and about 15 minutes on suspension one, two, and three, respectively. Duplicate 50 mL aliquots of each slurry suspension were independently inoculated with yeast, and cellulase at a concentration of 60 paper filter units "pfu" per gram cellulose, and the suspensions allowed to undergo simultaneous saccharification and fermentation for 7 days. Ethanol was measured by gas chromatography (GC) on the seventh day. The results for ethanol yields for Study 1 are shown in Table 2 and FIG. 7.

TABLE 2

Ethanol Yields from SSF Experiment

| Substrate | Treatment min | Final Ethanol g/l | Ethanol Yield g/g biomass | Max. Possible EtOH Yield g/g biomass | EtOH Efficiency % wt/wt |
|---|---|---|---|---|---|
| Switch Grass | 0 | 1.9 | 0.02 | 0.2 | 11.6% |
| Switch Grass | 5 | 4 | 0.05 | 0.2 | 24.4% |
| Switch Grass | 15 | 3.8 | 0.04 | 0.2 | 22.8% |

Results for Switch Grass Ethanol Yields

The ethanol yields in Table 2, were uniformly low, and achieved low percentages of maximum total theoretical ethanol yields (far right column). This indicated that the batch ultrasonic energy pretreatment of switch grass was not aggressive enough to promote optimal saccharification of cellulose. The inability to greatly increase the ethanol yield may be possibly attributable to 1) failure to remove or hydrolyze hemicellulose, which is a prerequisite for good cellulose digestion, or 2) failure to greatly swell and hydrate the cellulose to make it digestible. Nevertheless, pretreated samples of switch grass were approximately two-fold higher for final ethanol yields compared to the untreated sample (Table 2), which indicates that ultrasonic energy is creating a positive effect in terms of increasing cellulose digestibility. The switch grass results are also demonstrated in FIG. 7. The doubling of ethanol yields over the untreated control is viewed as a significantly positive result in terms of the utility for ultrasonic energy as an independent pretreatment technology, or as an enabling technology for existing pretreatment methods, especially given that the ultrasonic energy conditions and mechanical design are not optimized for maximal pretreatment efficacy in this study. In future studies, it is likely that more optimal ethanol yields may be achieved by use of a more aggressive, higher ultrasonic energy power, i.e., greater than 2 kilowatts, further including high power ultrasonic energy of at least about 3 kW or greater, or a different type of horn with respect to shape and size or a horn placed within a flow cell through which the fluid biomass slurry is directed as a continuous flow or counter flow, or some combination all of the above. In future studies, more optimal ethanol yields may also be achieved by integration of high power ultrasonic energy with existing biomass pretreatment methods such as dilute acid hydrolysis, high pressure hot water-based methods, i.e., hydrothermal treatments such as steam explosion and aqueous hot water extraction, reactor systems, ammonia explosion, ammonia recycled percolation, lime treatment, and other chemical treatments.

Study 2

A second study deployed batch process ultrasonic energy of crystalline cellulose (Sigmacell® Cellulose), with the addition of "Tween® 80," a non-ionic detergent purchased from Sigma-Aldrich, at a 1% final concentration. Tween® 80 is a surfactant which has detergent-like properties, and functions to improve the enzymatic digestibility of crystalline cellulose. The objective of the study was to determine if the presence of a surfactant such as Tween® 80, enabled ultrasonic energy to be a more effective pretreatment in terms of improving the digestibility of cellulose. Crystalline cellulose was suspended at 5% w/v solids in deionized water. Four suspension samples were made, and the final volume for each suspension was 500 mL. Ultrasonic energy treatments were for zero (0) minutes (control), and about 15 minutes. Two sets of samples were evaluated:

Set 1: No Addition of Tween® 80.

Samples 1 and 2 contained no Tween® 80. Sample 1 received no ultrasonic energy. Sample 2 received an approximately 15 minute treatment of ultrasonic energy. The glass beaker for sample 2 was held in an ice bath during the entire 15 minutes of ultrasonic energy to prevent high temperatures and shattering of the beaker.

Set 2: Tween® 80 Added to a 1% Final Concentration.

Samples 3 and 4 contained Tween® 80 at an approximately 1% final concentration. Sample 3 received no ultrasonic energy. Sample 4 received an approximately 15 minute treatment of ultrasonic energy. The glass beaker for sample 4 was held in an ice bath during the entire 15 minutes of ultrasonic energy to prevent high temperatures and shattering of the beaker.

After sonication, the four crystalline cellulose whole slurries from Sets 1 and 2 were immediately tested for cellulase digestibility, in a cellulose hydrolysis assay. This was performed by incubating duplicate aliquots all four whole slurry samples in the presence of a low cellulase loading (10 paper filter units "pfu" per gram cellulose), and a high cellulase loading (60 paper filter units "pfu" per gram cellulose) for approximately 72 hr, and measuring glucose released at about 4 hr, about 24 hr and about 72 hour time points. Glucose was quantitated by HPLC.

Results from Study 2

Figure 8:
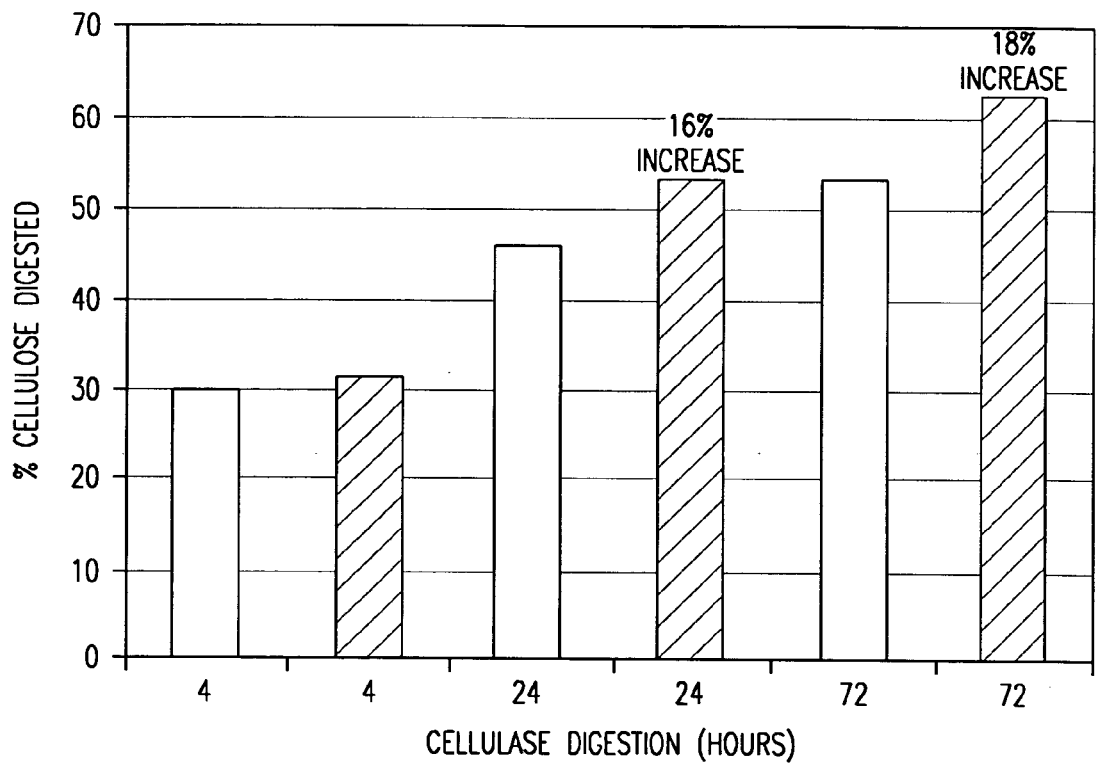
FIG. 8 is a graph showing percent cellulose digested versus hours of cellulase digestion for 10 paper filter units (pfu) of cellulase with about 15 minutes of sonication and no sonication in embodiments of the present invention.
Figure 9:
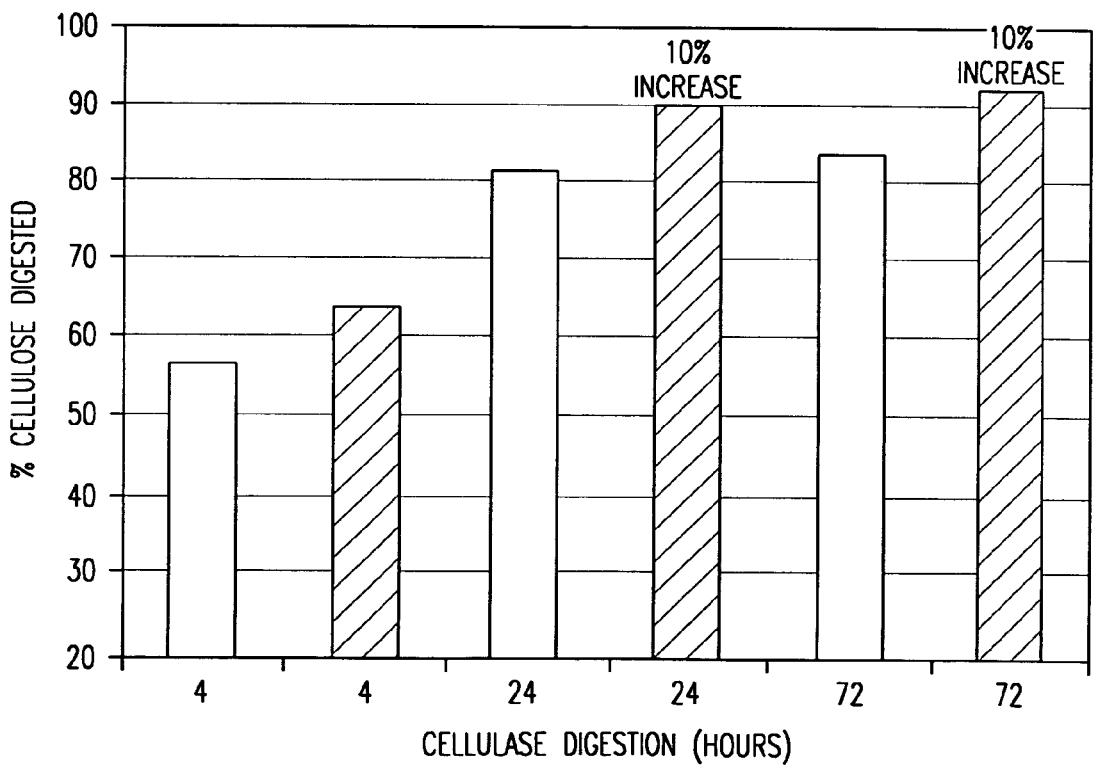
FIG. 9 is a graph showing percent cellulose digested versus hours of cellulase digestion for 60 paper filter units (pfu) of cellulase with about 15 minutes of sonication and no sonication in embodiments of the present invention.

The results for the Set 1 samples in which no Tween® 80 was added are shown in FIG. 8 and FIG. 9. The data is presented as percent of total cellulose digested as a function of the amount of glucose released. The plain bars indicate the percent of cellulose digested without ultrasonic energy, while the dashed bars are with approximately 15 minutes of ultrasonic energy. The graph depicted in FIG. 8 is the assay run with a low cellulase load (10 pfu/gm), while the graph depicted in FIG. 9 is the assay run with a high cellulase load (60 pfu/gm).

The results for the Set 1 samples with no added Tween® 80 indicate that an approximately 15 minute treatment of ultrasonic energy at 2 kilowatts and 20 kHz increased cellulose digestibility by about 16-18% under a low cellulase load, and by approximately 10% under a high cellulase dose, over the non-sonicated controls. It should also be kept in mind that 72 hours is a long digestion time, and that the 24 hour time point is a more "practical" time index. However, the 24 hour results with a low enzyme load are far from optimal in achieving maximum yields, even with the increase in digestibility due to ultrasonic energy pretreatment. Microscopic analysis of the approximately 15 minute sonicated sample showed that cellulose crystals were not significantly swelled or hydrated by the ultrasonic energy pretreatment. It is hypothesized that ultrasonic energy increased the affinity of the cellulase enzyme to the surface of the cellulose crystals, perhaps by creating a rougher surface, thereby enhancing the cellulose hydrolysis and release of glucose.

Figure 10:
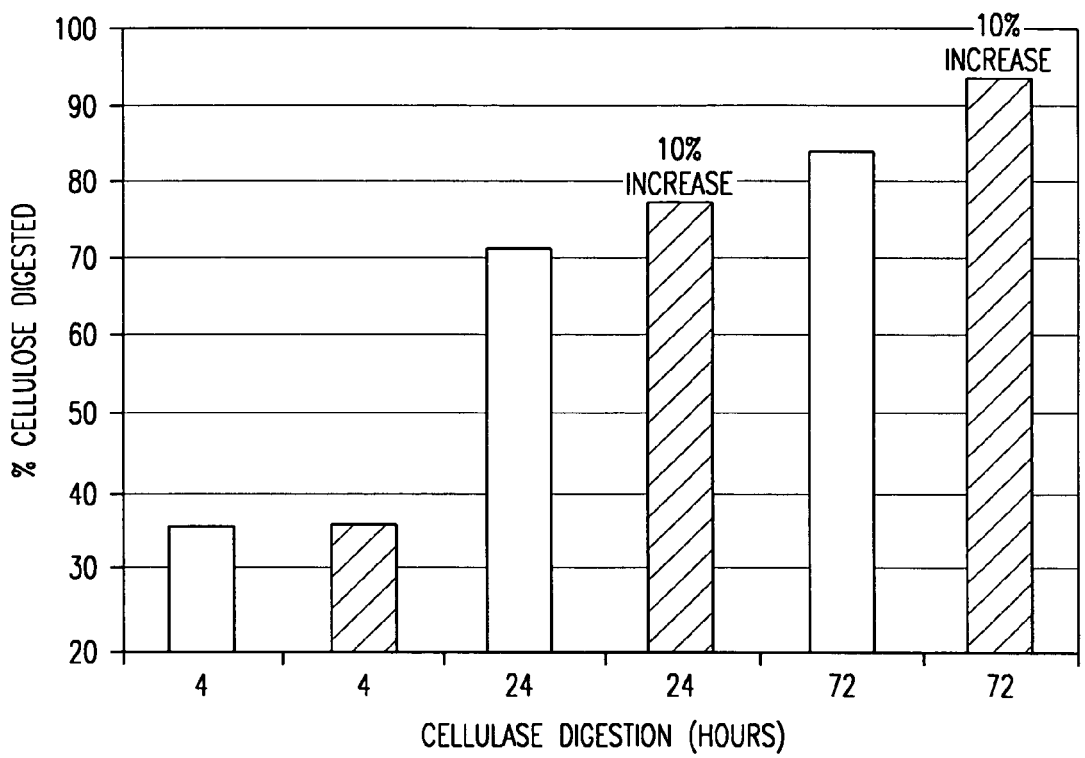
FIG. 10 is a graph showing percent cellulose digested versus hours of cellulase digestion for 10 paper filter units (pfu) of cellulose, with about 15 minutes of sonication and no sonication of cellulose in the presence of about 1% Tween® 80 brand surfactant in embodiments of the present invention.
Figure 11:
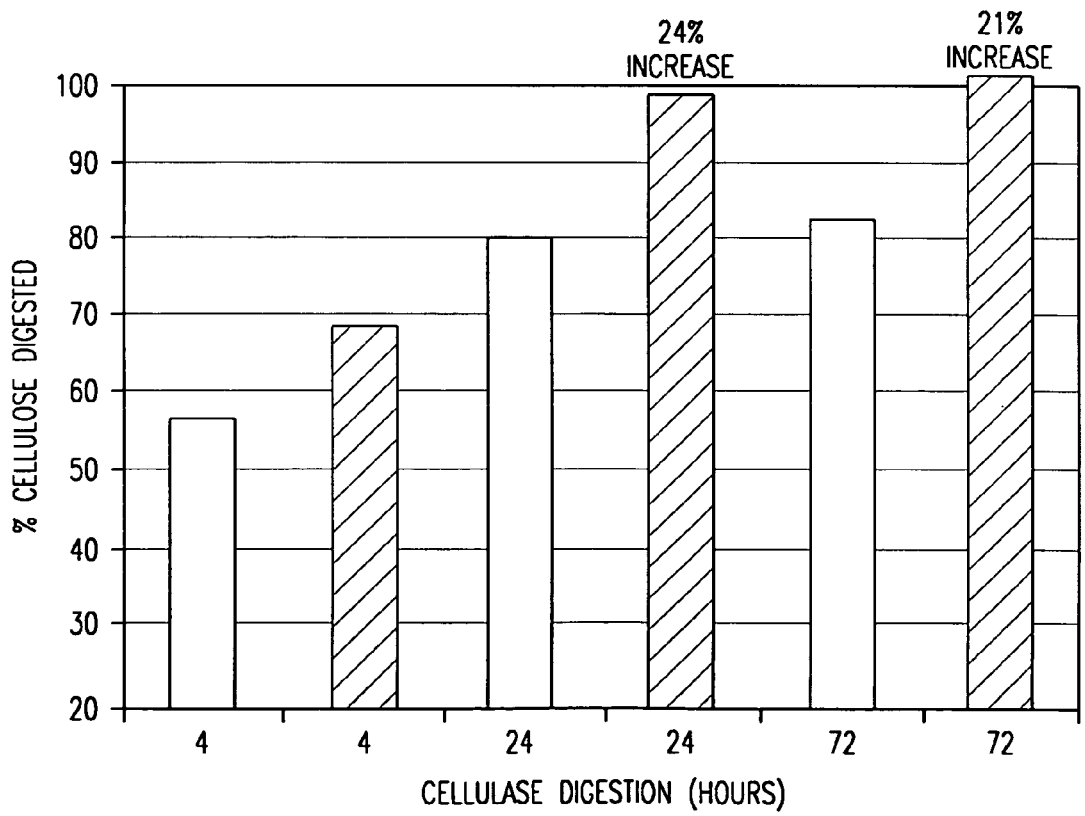
FIG. 11 is a graph showing percent cellulose digested versus hours of cellulase digestion for 60 paper filter units (pfu) of cellulose, with 15 minutes of sonication and no sonication of cellulose in the presence of about 1% Tween® 80 brand surfactant in embodiments of the present invention.

The results for the Set 2 samples in which Tween® 80 was added to a final concentration of approximately 1% are shown in FIG. 10 and FIG. 11. The data is presented as percent of total cellulose digested as a function of the amount of glucose released. The plain bars indicate the percent of cellulose digested without ultrasonic energy, while the dashed bars are with about 15 minutes of ultrasonic energy. The graph depicted in FIG. 10 is the assay run with a low cellulase load (10 pfu/gm), while the graph depicted in FIG. 11 is the assay run with a high cellulase load (60 pfu/gm).

The results for the second set of samples with no Tween® 80 indicate that an approximately 15 minute treatment of ultrasonic energy at about 2 kilowatts and about 20 kHz increased cellulose digestibility by 8-11% under a low cellulase load, and by 21-24% under a high cellulase dose, over the non-sonicated controls. Microscopic analysis of the sonicated sample with Tween® 80 showed that cellulose crystals were also not significantly swelled or hydrated by ultrasonic energy. Again, it is hypothesized that ultrasonic energy increased the affinity of the cellulase enzyme to the surface of the cellulose crystals, perhaps by creating a rougher surface, thereby enhancing the cellulose hydrolysis. Tween® 80 may have enhanced the disruption or disaggregation of the cellulose crystals at the surface during ultrasonic energy, which further facilitated enzymatic hydrolysis of cellulose.

The results in which Tween® 80 was present, and in which a high cellulase load was used, are highly meaningful, although not statistically significant simply because not enough samples were run in the test design. The presence of a surfactant such as Tween® 80 enhances the physical, mechanical disruption of crystalline cellulose by ultrasonic energy, such that the cellulose becomes much more digestible, as much as about 21-24% more digestible. The implications of employing a surfactant during ultrasonic energy are that ultrasonic energy may possibly function as a stand-alone pretreatment for biomass-to-ethanol processing. However, the implications are much greater that ultrasonic energy, with or without the presence of a surfactant such as Tween® 80, may more likely serve as an enabling technology that interfaces or integrates with an existing pretreatment technology, thereby optimizing or maximizing that particular pretreatment in terms of cellulose digestibility and ethanol yields. Future cellulose digestion studies may include integration of ultrasonic energy with existing biomass pretreatment methods such as dilute acid hydrolysis, high pressure hot water-based methods, i.e., hydrothermal treatments such as steam explosion and aqueous hot water extraction, reactor systems, ammonia explosion, ammonia recycled percolation, lime treatment, and other chemical treatments such as various surfactants similar in function to Tween® 80.

CONCLUSION

Application of ultrasonic energy to one or more of the various processing streams in a biomass to ethanol process can be accomplished with relatively minor retrofitting of equipment. Essentially, the ultrasonic transducer or transducers useful in the various embodiments of the present invention can be interfaced with or integrated into existing processing steps and technologies, thus allowing ethanol producers to overcome technological hurdles, inefficiencies, and poor yields in an easy and cost efficient manner without the need to undergo costly and time-consuming re-tooling of their facilities. Additionally, ultrasonic energy may potentially be used at any phase of other alcohol production processes to provide enhancements and benefits as described herein.

Various embodiments of the invention include process improvements enabled by the application of ultrasonic energy, including high powered ultrasonic (HPU) energy, at various points in the process of producing alcohol from biomass. As a result, economic barriers that are currently preventing the commercial implementation of biomass conversion technologies are reduced or eliminated.

The systems and methods of the present invention utilize ultrasonic energy at the frequencies and intensities required on an industrial scale to reduce the production cost of ethanol by improving biomass conversion per ton, reducing processing times for higher throughput, reducing operating costs, and increasing the marketability of co-products.

Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present subject matter. For example, ultrasonic energy is also useful for biomass-based production facilities which produce alcohols other than ethanol. Such alcohols include, but are not limited to, industrial alcohols such as methanol, isopropanol, butanol, and so forth, further including propane diol, which can be used to make bioplastics. It is also likely that ultrasonic energy would be useful in biomass-based production facilities that produce various organic acids, such as lactic acids. Most likely such production facilities which produce alcohols other than ethanol and/or organic acids consist of processes which utilize pretreatment technologies and fermentation processes described herein." Therefore, it is manifestly intended that embodiments of this invention be limited only by the claims and the equivalents thereof.

What is claimed is:

1. A method comprising:
   applying ultrasonic energy to a liquid medium processing stream in a cellulose-to-ethanol production process, wherein the liquid medium processing stream contains switch grass comprised of cellulose surrounded by a protective sheath of hemicellulose and lignin, wherein the ultrasonic energy is applied at one or more locations prior to fermentation, or before and after fermentation, with one or more high-powered transducers, each generating at least 3 kW of power and operating at a frequency of at least 17 kHz, wherein the power and frequency of the ultrasonic energy are sufficient to produce cavitational forces in the processing stream at an intensity and duration which causes at least a portion of the lignin to be loosened or removed from the cellulose, allowing an increased amount of cellulose to be hydrolyzed into one or more individual component sugars, wherein conversion of the one or more individual component sugars to one or more fermented individual component sugars during fermentation is increased; and
   distilling and dehydrating the one or more fermented individual component sugars to produce ethanol and residuals, wherein ethanol yield is increased by applying the ultrasonic energy.

2. The method of claim 1 further comprising pretreating the liquid medium processing stream with a high pressure hot water-based pretreatment, a reactor system pretreatment, ammonia explosion pretreatment, ammonia recycled percolation (ARP) pretreatment, lime pretreatment, pH-based pretreatment, or combinations thereof.

3. The method of claim 2 wherein at least one of the one or more locations is upstream of the pretreatment step, at the pretreatment step or immediately following the pretreatment step.

4. The method of claim 3 further comprising applying ultrasonic energy to the liquid medium processing stream downstream of the pretreatment step with one or more additional transducers, wherein the one or more additional transducers are high-powered transducers, transducers operating at less than high power, or a combination thereof, further wherein at least one of the one or more additional transducers operate at a level which is not sufficient to produce cavitational forces.

5. The method of claim 1 wherein the hemicellulose is predominantly xylose.

6. The method of claim 3 wherein there is also an increased conversion of hemicellulose into one or more individual component sugars.

7. The method of claim 3 wherein the cellulose is hydrolyzed and saccharified with acid and the process further comprises:
   separating the individual component sugars and the acid to produce one or more separated individual component sugars;
   neutralizing the one or more individual component sugars to produce one or more neutralized individual component sugars which are fermented with yeast to produce the one or more fermented individual component sugars.

8. The method of claim 1 further comprising centrifuging the residuals to produce thin stillage.

9. The method of claim 8 further comprising applying sonication to the thin stillage to kill fermentative recombinant microorganisms.

10. The method of claim 3 wherein the cellulose is hydrolyzed and saccharified with acid and the process further comprises:
    separating the individual component sugars and the acid to produce one or more separated individual component sugars;
    neutralizing the one or more individual component sugars to produce one or more neutralized individual component sugars which are fermented with bacteria to produce the one or more fermented individual component sugar.

11. The method of claim 8 further comprising applying sonication to the thin stillage to cause any transgenic nucleic acids present to be altered by degradation, depolymerization, denaturation or any combination thereof.

12. The method of claim 1 further comprising pretreating the liquid medium processing stream with a dilute acid hydrolysis pretreatment.

* * * * *

UNITED STATES PATENT AND TRADEMARK OFFICE
CERTIFICATE OF CORRECTION

| | | |
|---|---|---|
| PATENT NO. | : 7,504,245 B2 | |
| APPLICATION NO. | : 10/954657 | |
| DATED | : March 17, 2009 | |
| INVENTOR(S) | : Kinley et al. | |

It is certified that error appears in the above-identified patent and that said Letters Patent is hereby corrected as shown below:

On Page 2, under "Other Publications", in column 2, line 36, delete "Theorectical" and insert -- Theoretical --, therefor.

In column 3, line 34, after "power" delete "and".

In column 8, line 44, delete "Iowa.," and insert -- Iowa, --, therefor.

In column 8, line 48, delete "vandium" and insert -- vanadium --, therefor.

In column 10, line 34, delete "fingus" and insert -- fungus --, therefor.

In column 10, line 41, delete "Heilscher" and insert -- Hielscher --, therefor.

In column 10, line 51, delete "Heilscher" and insert -- Hielscher --, therefor.

In column 10, line 64, delete "Heilscher" and insert -- Hielscher --, therefor.

In column 12, line 11, delete "higher" and insert-- high --, therefor.

Signed and Sealed this

Sixteenth Day of June, 2009

JOHN DOLL
*Acting Director of the United States Patent and Trademark Office*